US011460696B2

(12) United States Patent
Jenabzadeh

(10) Patent No.: US 11,460,696 B2
(45) Date of Patent: Oct. 4, 2022

(54) HEAD-MOUNTABLE APPARATUS AND METHODS

(71) Applicant: Sony Interactive Entertainment Inc., Tokyo (JP)

(72) Inventor: Mandana Jenabzadeh, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 158 days.

(21) Appl. No.: 16/754,258

(22) PCT Filed: Nov. 15, 2018

(86) PCT No.: PCT/GB2018/053309
§ 371 (c)(1),
(2) Date: Apr. 7, 2020

(87) PCT Pub. No.: WO2019/115994
PCT Pub. Date: Jun. 20, 2019

(65) Prior Publication Data
US 2020/0319457 A1 Oct. 8, 2020

(30) Foreign Application Priority Data
Dec. 13, 2017 (GB) .................................... 1720756

(51) Int. Cl.
*G02B 27/01* (2006.01)
*A61B 5/16* (2006.01)
(Continued)

(52) U.S. Cl.
CPC .............. *G02B 27/017* (2013.01); *A61B 5/11* (2013.01); *A61B 5/163* (2017.08); *A61B 5/4094* (2013.01);
(Continued)

(58) Field of Classification Search
CPC ............ G02B 27/017; G02B 2027/014; G02B 2027/0187; A61B 5/11; A61B 5/163;
(Continued)

(56) References Cited

U.S. PATENT DOCUMENTS

| 11,039,780 B2* | 6/2021 | Krauss | ................... A61B 5/746 |
| 2008/0319276 A1* | 12/2008 | Jung | ....................... G16H 50/20 |
| | | | 600/300 |

(Continued)

FOREIGN PATENT DOCUMENTS

| WO | 2015030797 A1 | 3/2015 |
| WO | 2018063521 A1 | 4/2018 |

OTHER PUBLICATIONS

International Search Report and Written Opinion for corresponding PCT Application No. PCT/GB2018/053309, 18 pages, dated Feb. 19, 2019.

(Continued)

*Primary Examiner* — Jason M Mandeville
(74) *Attorney, Agent, or Firm* — Matthew B. Dernier, Esq.

(57) ABSTRACT

A method of assisting a user wearing a head mountable display (HMD) when determining that the user may be in a pathological state includes: detecting, by one or more sensors, one or more parameters indicating one or more current properties of the user, generating information indicating the one or more current properties of the user based on the one or more parameters, determining whether the user may be in a pathological state or a non-pathological state based on the information indicating one or more of the current properties of the user, and performing a process under instruction of a processor in response to determining that the user may be in a pathological state, the process comprising one or more
(Continued)

operations that the user can voluntarily instruct when the user is in a non-pathological state.

16 Claims, 16 Drawing Sheets

(51) Int. Cl.
    *A61B 5/11*     (2006.01)
    *A61B 5/00*     (2006.01)
    *G06F 3/01*     (2006.01)
    *G16H 50/20*     (2018.01)
    *G16H 40/63*     (2018.01)

(52) U.S. Cl.
    CPC .......... *A61B 5/6803* (2013.01); *G06F 3/012* (2013.01); *G06F 3/013* (2013.01); *G02B 2027/014* (2013.01); *G02B 2027/0187* (2013.01); *G06F 3/011* (2013.01); *G06F 2203/011* (2013.01); *G16H 40/63* (2018.01); *G16H 50/20* (2018.01)

(58) Field of Classification Search
    CPC ... A61B 5/4094; A61B 5/6803; A61B 5/6814; G06F 3/011; G06F 3/012; G06F 3/013; G06F 3/015; G06F 2203/011; G16H 50/20; G16H 40/63
    USPC ........................................................ 345/7–8
    See application file for complete search history.

(56) References Cited

U.S. PATENT DOCUMENTS

| | | | |
|---|---|---|---|
| 2011/0035254 A1* | 2/2011 | Ho | G06F 16/9535 705/7.29 |
| 2012/0223833 A1* | 9/2012 | Thomas | G16H 50/30 340/539.12 |
| 2014/0316192 A1 | 10/2014 | De Zamotti | |
| 2015/0223731 A1 | 8/2015 | Sahin | |
| 2016/0022167 A1* | 1/2016 | Simon | A61B 5/378 600/301 |
| 2016/0178904 A1 | 6/2016 | Deleeuw | |
| 2017/0007111 A1 | 1/2017 | Samec | |
| 2017/0095157 A1 | 4/2017 | Tzvieli | |

OTHER PUBLICATIONS

Y.H. Nam et al: "Automatic detection of nausea using bio-signals during immersion in a virtual reality environment" 2014 36th Annual International Conference of the IEEE Engineering in Medicine and Biology Society, pp. 2013-2015, Oct. 25, 2001.

Combined Search and Examination Report for corresponding GB 1720756.4, 5 pages, dated May 31, 2018.

* cited by examiner

HEAD-MOUNTABLE APPARATUS AND METHODS

BACKGROUND

Field of the Disclosure

This disclosure relates to a head mountable apparatus and methods.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

A head-mountable display (HMD) is one example of a head-mountable apparatus for use in a virtual reality system in which an HMD wearer views a virtual environment. In an HMD, an image or video display device is provided which may be worn on the head or as part of a helmet. Either one eye or both eyes are provided with small electronic display devices.

Although the original development of HMDs and virtual reality was perhaps driven by the military and professional applications of these devices, HMDs are becoming more popular for use by casual users in, for example, computer game or domestic computing applications.

The techniques to be discussed are applicable to individual three-dimensional images or to video signals comprising successive three-dimensional images. Therefore, references to "images" in the discussion below should be taken to encompass the use of the same techniques in respect of video signals.

The foregoing paragraphs have been provided by way of general introduction, and are not intended to limit the scope of the following claims. The described embodiments, together with further advantages, will be best understood by reference to the following detailed description taken in conjunction with the accompanying drawings.

SUMMARY

An example embodiment provides a method of assisting a user wearing a head mountable display (HMD) when determining that the user may be in a pathological state, the method comprising the steps of detecting, by one or more sensors, one or more parameters indicating one or more current properties of the user, generating information indicating the one or more current properties of the user based on the one or more parameters, determining whether the user may be in a pathological state or a non-pathological state based on the information indicating one or more of the current properties of the user, and performing a process under instruction of a processor in response to determining that the user may be in a pathological state, the process comprising one or more operations that the user can voluntarily instruct when the user is in a non-pathological state.

Another example embodiment provides computer software which, when executed by a computer, causes the computer to perform the steps of the method defined above.

Example embodiments provide a machine-readable, non-transitory storage medium which stores such computer software.

Another example embodiment provides an apparatus for assisting a user wearing a head mountable display (HMD) when determining that the user may be in a pathological state, the apparatus comprising: one or more sensors configured to detect one or more parameters indicating one or more current properties of the user, a processor configured to generate information indicating the one or more current properties of the user based on the one or more parameters and to determine whether the user may be in a pathological state or a non-pathological state based on the information, and an HMD configured to perform a process under instruction of the processor in response to determining that the user may be in a pathological state, the process comprising one or more operations that the user can voluntarily instruct when the user's body is in a non-pathological state.

Various other aspects and features of the present disclosure are defined in the appended claims and within the text of the accompanying description and include at least a head mountable apparatus such as a display and a method of operating a head-mountable apparatus as well as a computer program.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1:
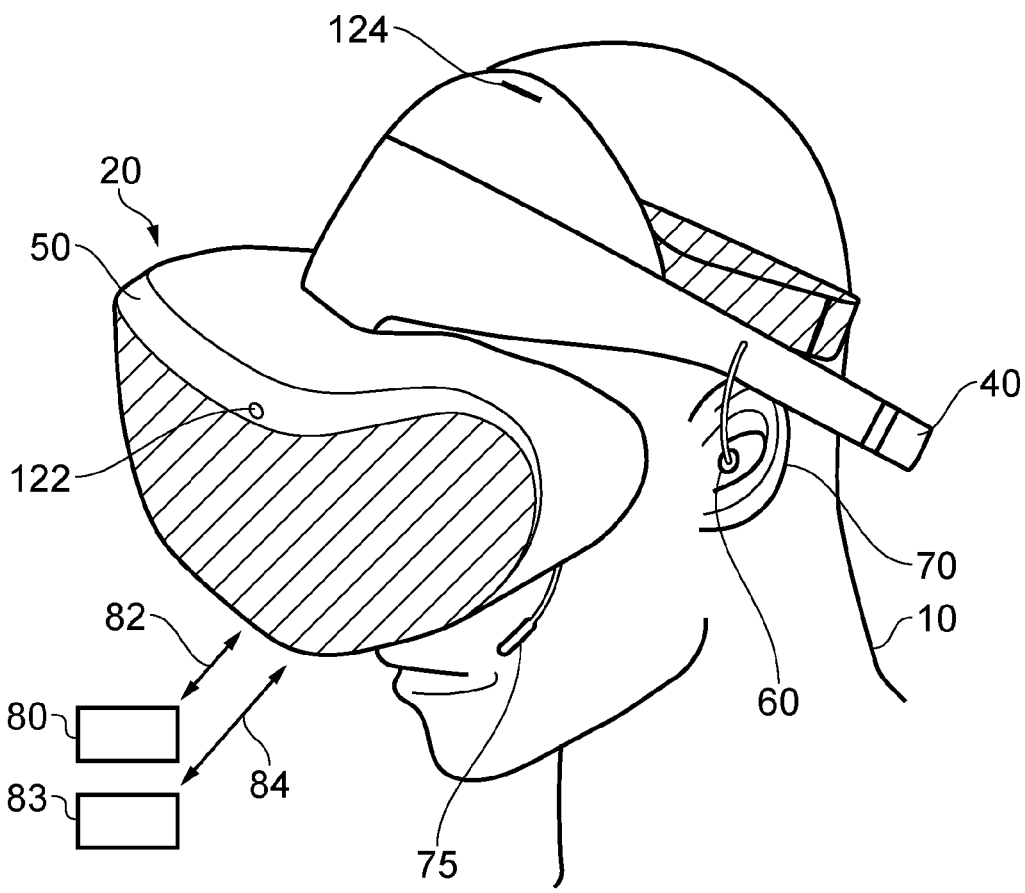
FIG. 1 schematically illustrates an HMD worn by a user.

Referring now to FIG. 1, a user 10 is wearing an HMD 20 (as an example of a generic head-mountable apparatus or virtual reality apparatus). The HMD comprises a frame 40, in this example formed of a rear strap and a top strap, and a display portion 50.

Note that the HMD of FIG. 1 may comprise further features, to be described below in connection with other drawings, but which are not shown in FIG. 1 for clarity of this initial explanation.

The HMD of FIG. 1 completely (or at least substantially completely) obscures the user's view of the surrounding environment. All that the user can see is the pair of images displayed within the HMD.

The HMD has associated headphone audio transducers or earpieces 60 which fit into the user's left and right ears 70. The earpieces 60 replay an audio signal provided from an external source, which may be the same as the video signal source which provides the video signal for display to the user's eyes. A boom microphone 75 is mounted on the HMD so as to extend towards the user's mouth.

The combination of the fact that the user can see only what is displayed by the HMD and, subject to the limitations of the noise blocking or active cancellation properties of the earpieces and associated electronics, can hear only what is provided via the earpieces, mean that this HMD may be considered as a so-called "full immersion" HMD. Note however that in some embodiments the HMD is not a full immersion HMD, and may provide at least some facility for the user to see and/or hear the user's surroundings. This could be by providing some degree of transparency or partial transparency in the display arrangements, and/or by projecting a view of the outside (captured using a camera, for example a camera mounted on the HMD) via the HMD's displays, and/or by allowing the transmission of ambient sound past the earpieces and/or by providing a microphone to generate an input sound signal (for transmission to the earpieces) dependent upon the ambient sound.

A front-facing camera 122 may capture images to the front of the HMD, in use. A Bluetooth® antenna 124 may provide communication facilities or may simply be arranged as a directional antenna to allow a detection of the direction of a nearby Bluetooth transmitter.

In operation, a video signal is provided for display by the HMD. This could be provided by an external video signal source 80 such as a video games machine or data processing apparatus (such as a personal computer), in which case the signals could be transmitted to the HMD by a wired or a wireless connection 82. Examples of suitable wireless connections include Bluetooth® connections. Audio signals for the earpieces 60 can be carried by the same connection. Similarly, any control signals passed from the HMD to the video (audio) signal source may be carried by the same connection. Furthermore, a power supply 83 (including one or more batteries and/or being connectable to a mains power outlet) may be linked by a cable 84 to the HMD. Note that the power supply 83 and the video signal source 80 may be separate units or may be embodied as the same physical unit. There may be separate cables for power and video (and indeed for audio) signal supply, or these may be combined for carriage on a single cable (for example, using separate conductors, as in a USB cable, or in a similar way to a "power over Ethernet" arrangement in which data is carried as a balanced signal and power as direct current, over the same collection of physical wires). The video and/or audio signal may be carried by, for example, an optical fibre cable. In other embodiments, at least part of the functionality associated with generating image and/or audio signals for presentation to the user may be carried out by circuitry and/or processing forming part of the HMD itself. A power supply may be provided as part of the HMD itself.

Some embodiments of the disclosure are applicable to an HMD having at least one electrical and/or optical cable linking the HMD to another device, such as a power supply and/or a video (and/or audio) signal source. So, embodiments of the disclosure can include, for example:

(a) an HMD having its own power supply (as part of the HMD arrangement) but a cabled connection to a video and/or audio signal source;

(b) an HMD having a cabled connection to a power supply and to a video and/or audio signal source, embodied as a single physical cable or more than one physical cable;

(c) an HMD having its own video and/or audio signal source (as part of the HMD arrangement) and a cabled connection to a power supply;

(d) an HMD having a wireless connection to a video and/or audio signal source and a cabled connection to a power supply; or (e) an HMD having its own video and/or audio signal source and its own power supply (both as part of the HMD arrangement).

If one or more cables are used, the physical position at which the cable 82 and/or 84 enters or joins the HMD is not particularly important from a technical point of view. Aesthetically, and to avoid the cable(s) brushing the user's face in operation, it would normally be the case that the cable(s) would enter or join the HMD at the side or back of the HMD (relative to the orientation of the user's head when worn in normal operation). Accordingly, the position of the cables 82, 84 relative to the HMD in FIG. 1 should be treated merely as a schematic representation.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other (not full immersion) examples, the user's view of the external environment may not in fact be entirely obscured; the displayed images could be arranged so as to be superposed (from the user's point of view) over the external environment. An example of such an arrangement will be described below with reference to FIG. 4.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160. The way in which the display element and the optical element(s) cooperate to provide a display to the user will be described with reference to FIG. 3.

Figure 3:
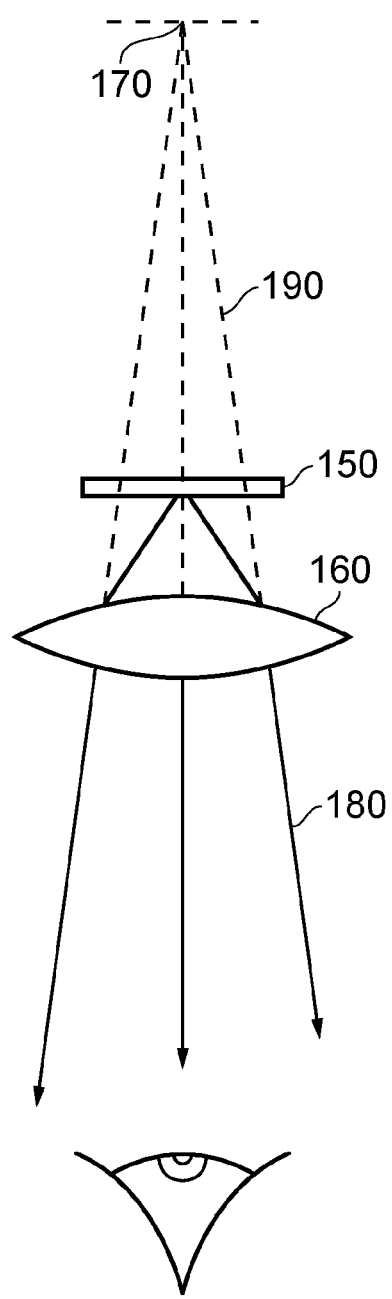
FIG. 3 schematically illustrates the formation of a virtual image by an HMD.

Referring to FIG. 3, the display element 150 generates a displayed image which is (in this example) refracted by the optical elements 160 (shown schematically as a convex lens but which could include compound lenses or other elements) so as to generate a virtual image 170 which appears to the user to be larger than and significantly further away than the real image generated by the display element 150. As an example, the virtual image may have an apparent image size (image diagonal) of more than 1 m and may be disposed at a distance of more than 1 m from the user's eye (or from the frame of the HMD). In general terms, depending on the purpose of the HMD, it is desirable to have the virtual image disposed a significant distance from the user. For example, if the HMD is for viewing movies or the like, it is desirable that the user's eyes are relaxed during such viewing, which requires a distance (to the virtual image) of at least several metres. In FIG. 3, solid lines (such as the line 180) are used to denote real optical rays, whereas broken lines (such as the line 190) are used to denote virtual rays.

Figure 4:
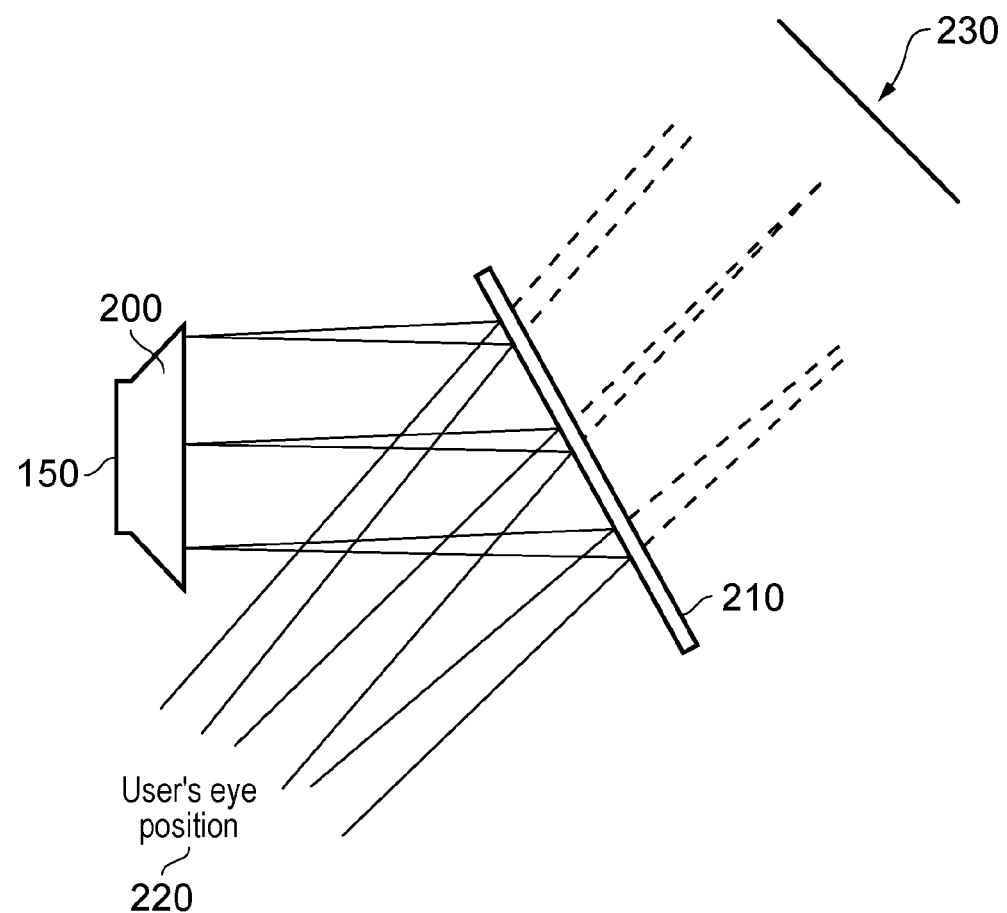
FIG. 4 schematically illustrates another type of display for use in an HMD.

An alternative arrangement is shown in FIG. 4. This arrangement may be used where it is desired that the user's view of the external environment is not entirely obscured. However, it is also applicable to HMDs in which the user's external view is wholly obscured. In the arrangement of FIG. 4, the display element 150 and optical elements 200 cooperate to provide an image which is projected onto a mirror 210, which deflects the image towards the user's eye position 220. The user perceives a virtual image to be located at a position 230 which is in front of the user and at a suitable distance from the user.

In the case of an HMD in which the user's view of the external surroundings is entirely obscured, the mirror 210 can be a substantially 100% reflective mirror. The arrangement of FIG. 4 then has the advantage that the display element and optical elements can be located closer to the centre of gravity of the user's head and to the side of the user's eyes, which can produce a less bulky HMD for the user to wear. Alternatively, if the HMD is designed not to completely obscure the user's view of the external environment, the mirror 210 can be made partially reflective so that the user sees the external environment, through the mirror 210, with the virtual image superposed over the real external environment.

Figure 5:
FIG. 5 schematically illustrates a pair of stereoscopic images.

In the case where separate respective displays are provided for each of the user's eyes, it is possible to display stereoscopic images. An example of a pair of stereoscopic images for display to the left and right eyes is shown in FIG. 5. The images exhibit a lateral displacement relative to one another, with the displacement of image features depending upon the (real or simulated) lateral separation of the cameras by which the images were captured, the angular convergence of the cameras and the (real or simulated) distance of each image feature from the camera position.

Note that the lateral displacements in FIG. 5 could in fact be the other way round, which is to say that the left eye image as drawn could in fact be the right eye image, and the right eye image as drawn could in fact be the left eye image. This is because some stereoscopic displays tend to shift objects to the right in the right eye image and to the left in the left eye image, so as to simulate the idea that the user is looking through a stereoscopic window onto the scene beyond. However, some HMDs use the arrangement shown in FIG. 5 because this gives the impression to the user that the user is viewing the scene through a pair of binoculars. The choice between these two arrangements is at the discretion of the system designer.

In some situations, an HMD may be used simply to view movies and the like. In this case, there is no change required to the apparent viewpoint of the displayed images as the user turns the user's head, for example from side to side. In other uses, however, such as those associated with virtual reality (VR) or augmented reality (AR) systems, the user's viewpoint needs to track movements with respect to a real or virtual space in which the user is located.

Figure 6:
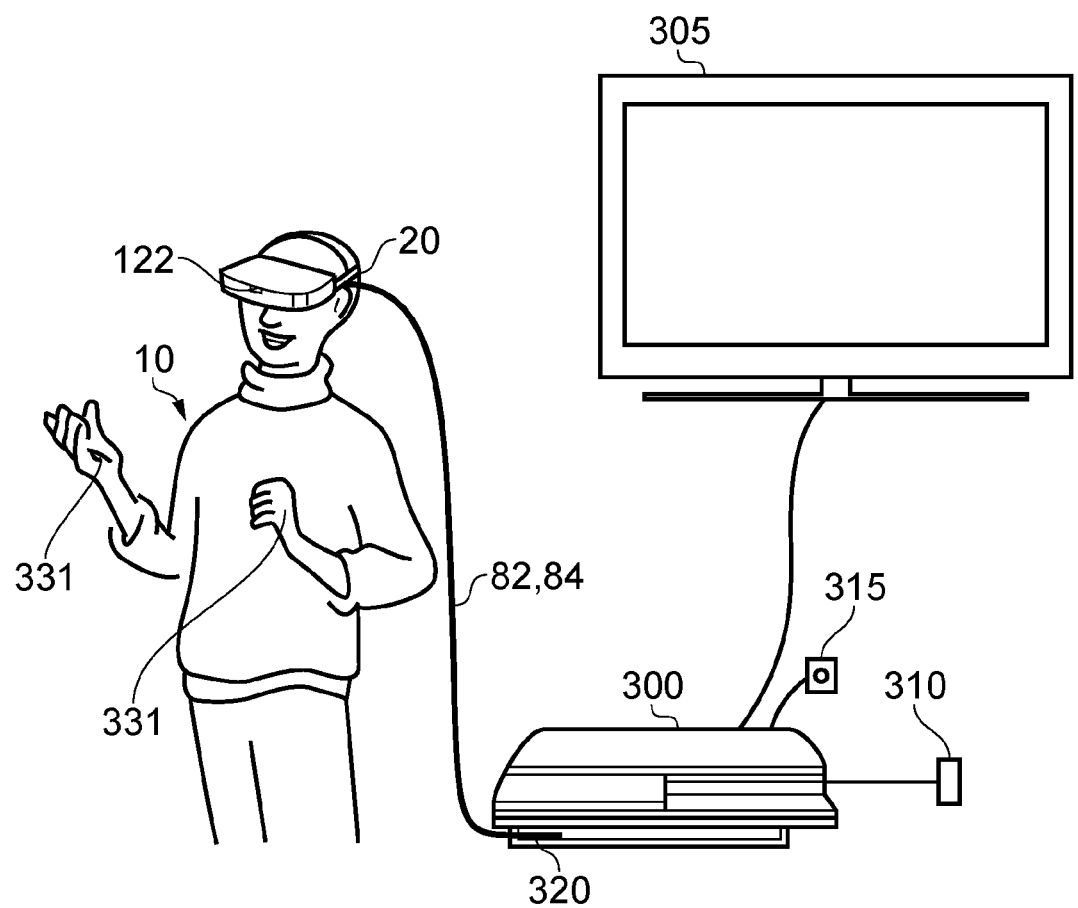
FIGS. 6 and 7 schematically illustrate a user wearing an HMD connected to a Sony® PlayStation 3® games console.

FIG. 6 schematically illustrates an example virtual reality system and in particular shows a user wearing an HMD connected to a Sony® PlayStation 3® games console 300 as an example of a base device. The games console 300 is connected to a mains power supply 310 and (optionally) to a main display screen (not shown). A cable, acting as the cables 82, 84 discussed above (and so acting as both power supply and signal cables), links the HMD 20 to the games console 300 and is, for example, plugged into a USB socket 320 on the console 300. Note that in the present embodiments, a single physical cable is provided which fulfils the functions of the cables 82, 84.

The video displays in the HMD 20 are arranged to display images generated by the games console 300, and the earpieces 60 in the HMD 20 are arranged to reproduce audio signals generated by the games console 300. Note that if a USB type cable is used, these signals will be in digital form when they reach the HMD 20, such that the HMD 20 comprises a digital to analogue converter (DAC) to convert at least the audio signals back into an analogue form for reproduction.

Images from the camera 122 mounted on the HMD 20 are passed back to the games console 300 via the cable 82, 84. Similarly, if motion or other sensors are provided at the HMD 20, signals from those sensors may be at least partially processed at the HMD 20 and/or may be at least partially processed at the games console 300. The use and processing of such signals will be described further below.

The USB connection from the games console 300 also provides power to the HMD 20, according to the USB standard.

FIG. 6 also shows a separate display 305 such as a television or other openly viewable display (by which it is meant that viewers other than the HMD wearer may see images displayed by the display 305) and a camera 315, which may be (for example) directed towards the user (such as the HMD wearer) during operation of the apparatus. An example of a suitable camera is the PlayStation Eye camera, although more generally a generic "webcam", connected to the console 300 by a wired (such as a USB) or wireless (such as WiFi or Bluetooth) connection.

The display 305 may be arranged (under the control of the games console) to provide the function of a so-called "social screen". It is noted that playing a computer game using an HMD can be very engaging for the wearer of the HMD but less so for other people in the vicinity (particularly if they are not themselves also wearing HMDs). To provide an improved experience for a group of users, where the number of HMDs in operation is fewer than the number of users, images can be displayed on a social screen. The images displayed on the social screen may be substantially similar to those displayed to the user wearing the HMD, so that viewers of the social screen see the virtual environment (or a subset, version or representation of it) as seen by the HMD wearer. In other examples, the social screen could display other material such as information relating to the HMD wearer's current progress through the ongoing computer game. For example, the HMD wearer could see the game environment from a first person viewpoint whereas the social screen could provide a third person view of activities and movement of the HMD wearer's avatar, or an overview of a larger portion of the virtual environment. In these examples, an image generator (for example, a part of the functionality of the games console) is configured to generate some of the virtual environment images for display by a display separate to the head mountable display.

In FIG. 6 the user is wearing one or two so-called haptic gloves 331. These can include actuators to provide haptic feedback to the user, for example under the control of processing carried out by the console 300. They may also provide configuration and/or location sensing.

Note that other haptic interfaces can be used, providing one or more actuators and/or one or more sensors. For example, a so-called haptics suit may be worn by the user. Haptic shoes may include one or more actuators and one or more sensors. Or the user could stand on or hold a haptic interface device. The one or more actuators associated with these devices may have different respective frequency responses and available amplitudes of vibration. Therefore in example arrangements to be discussed below the haptic generator can be responsive to attributes defining one or capabilities of the haptic interface. In some examples, an attribute defines a frequency response of the haptic interface. In some examples, an attribute defines a maximum amplitude which may be represented by the haptic interface.

Figure 7:
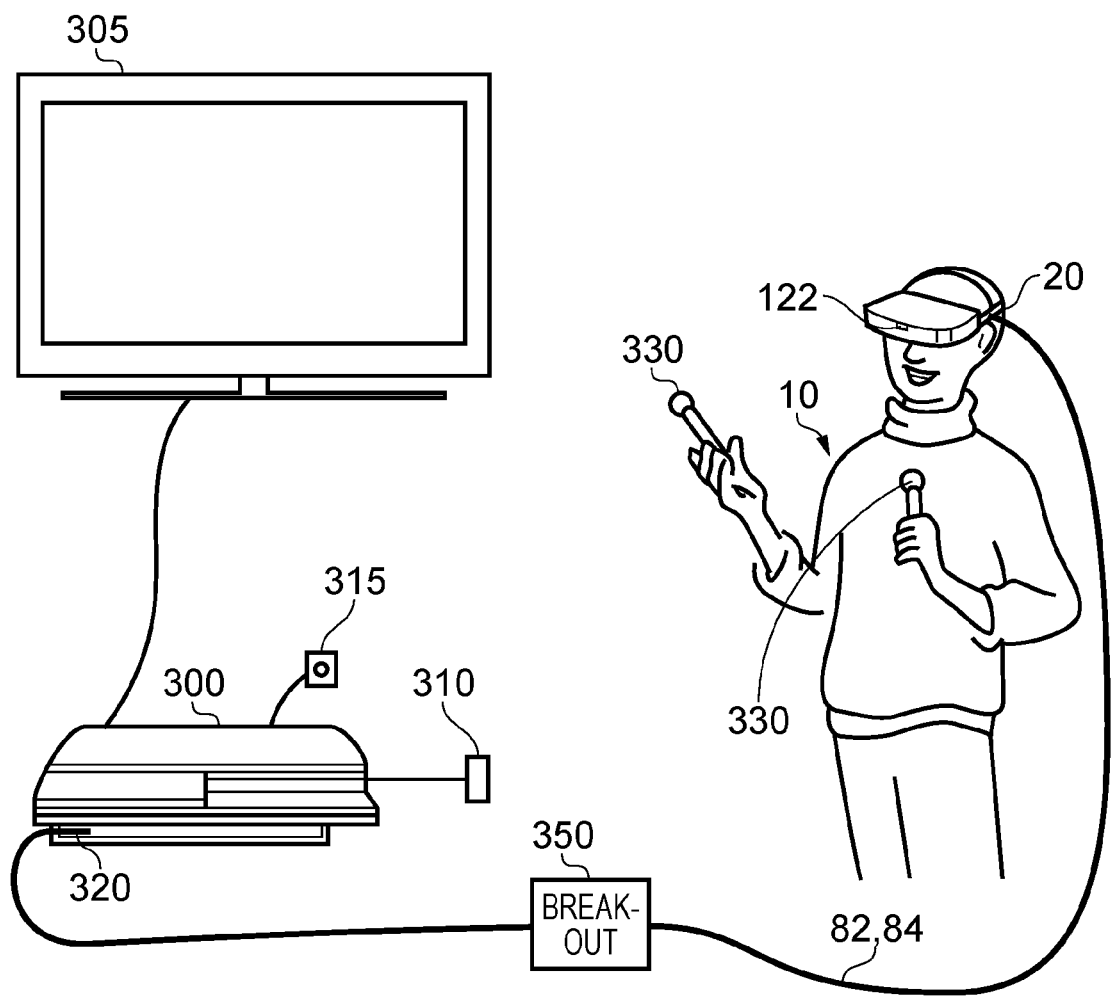

FIG. 7 schematically illustrates a similar arrangement (another example of a virtual reality system) in which the games console is connected (by a wired or wireless link) to a so-called "break out box" acting as a base or intermediate device 350, to which the HMD 20 is connected by a cabled link 82, 84. The breakout box has various functions in this regard. One function is to provide a location, near to the user, for some user controls relating to the operation of the HMD, such as (for example) one or more of a power control, a brightness control, an input source selector, a volume control and the like. Another function is to provide a local power supply for the HMD (if one is needed according to the embodiment being discussed). Another function is to provide a local cable anchoring point. In this last function, it is not envisaged that the break-out box 350 is fixed to the ground or to a piece of furniture, but rather than having a very long trailing cable from the games console 300, the break-out box provides a locally weighted point so that the cable 82, 84 linking the HMD 20 to the break-out box will tend to move around the position of the break-out box. This can improve user safety and comfort by avoiding the use of very long trailing cables.

In FIG. 7, the user is also shown holding a pair of hand-held controller 330s which may be, for example, Sony® Move® controllers which communicate wirelessly with the games console 300 to control (or to contribute to the control of) game operations relating to a currently executed game program. The user may also be wearing one or two haptic gloves as discussed in connection with FIG. 6.

It will be appreciated that the localisation of processing in the various techniques described in this application can be varied without changing the overall effect, given that an HMD may form part of a set or cohort of interconnected devices (that is to say, interconnected for the purposes of data or signal transfer, but not necessarily connected by a physical cable). So, processing which is described as taking place "at" one device, such as at the HMD, could be devolved to another device such as the games console (base device) or the break-out box. Processing tasks can be shared amongst devices. Source signals, on which the processing is to take place, could be distributed to another device, or the processing results from the processing of those source signals could be sent to another device, as required. So any references to processing taking place at a particular device should be understood in this context. Similarly, where an interaction between two devices is basically symmetrical, for example where a camera or sensor on one device detects a signal or feature of the other device, it will be understood that unless the context prohibits this, the two devices could be interchanged without any loss of functionality.

As mentioned above, in some uses of the HMD, such as those associated with virtual reality (VR) or augmented reality (AR) systems, the user's viewpoint needs to track movements with respect to a real or virtual space in which the user is located.

This tracking is carried out by detecting motion of the HMD and varying the apparent viewpoint of the displayed images so that the apparent viewpoint tracks the motion.

Figure 8:
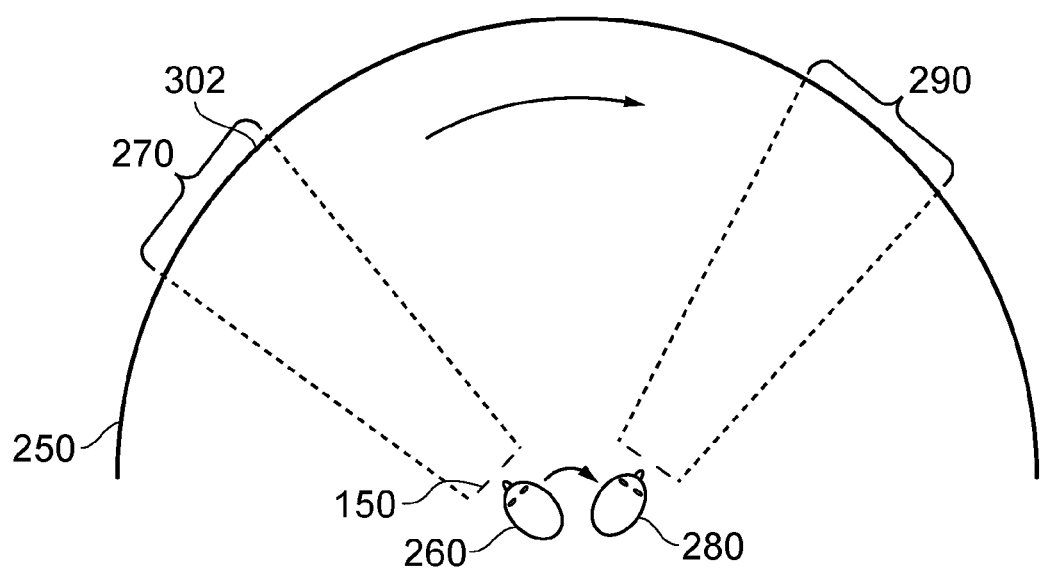
FIG. 8 schematically illustrates a change of view of user of an HMD.

FIG. 8 schematically illustrates the effect of a user head movement in a VR or AR system.

Referring to FIG. 8, a virtual environment is represented by a (virtual) spherical shell 250 around a user. This provides an example of a virtual display screen (VDS). Because of the need to represent this arrangement on a two-dimensional paper drawing, the shell is represented by a part of a circle, at a distance from the user equivalent to the separation of the displayed virtual image from the user. A user is initially at a first position 260 and is directed towards a portion 270 of the virtual environment. It is this portion 270 which is represented in the images displayed on the display elements 150 of the user's HMD. It can be seen from the drawing that the VDS subsists in three dimensional space (in a virtual sense) around the position in space of the HMD wearer, such that the HMD wearer sees a current portion of the VDS according to the HMD orientation.

Consider the situation in which the user then moves his head to a new position and/or orientation 280. In order to maintain the correct sense of the virtual reality or augmented reality display, the displayed portion of the virtual environment also moves so that, at the end of the movement, a new portion 290 is displayed by the HMD.

So, in this arrangement, the apparent viewpoint within the virtual environment moves with the head movement. If the head rotates to the right side, for example, as shown in FIG. 8, the apparent viewpoint also moves to the right from the user's point of view. If the situation is considered from the aspect of a displayed object, such as a displayed object 300, this will effectively move in the opposite direction to the head movement. So, if the head movement is to the right, the apparent viewpoint moves to the right but an object such as the displayed object 300 which is stationary in the virtual environment will move towards the left of the displayed image and eventually will disappear off the left-hand side of the displayed image, for the simple reason that the displayed portion of the virtual environment has moved to the right whereas the displayed object 300 has not moved in the virtual environment.

Figure 2:
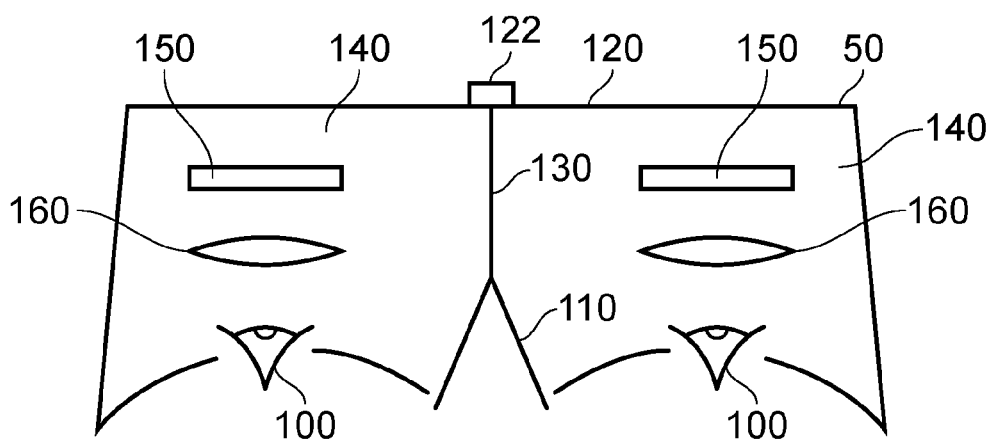
FIG. 2 is a schematic plan view of an HMD.
Figure 9A:
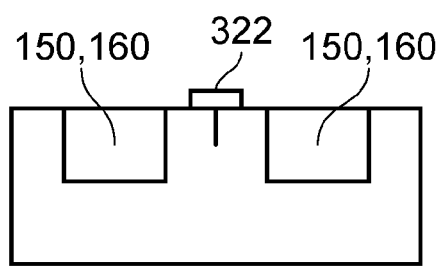
FIGS. 9a and 9b schematically illustrate HMDs with motion sensing.
Figure 9B:
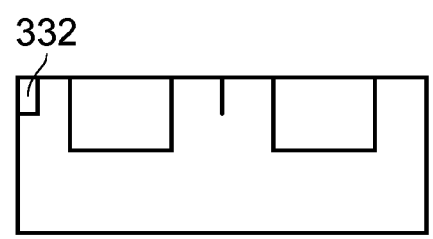

FIGS. 9a and 9b schematically illustrated HMDs with motion sensing. The two drawings are in a similar format to that shown in FIG. 2. That is to say, the drawings are schematic plan views of an HMD, in which the display element 150 and optical elements 160 are represented by a simple box shape. Many features of FIG. 2 are not shown, for clarity of the diagrams. Both drawings show examples of HMDs with a motion detector for detecting motion of the observer's head.

In FIG. 9a, a forward-facing camera 322 is provided on the front of the HMD. This may be the same camera as the camera 122 discussed above, or may be an additional camera. This does not necessarily provide images for display to the user (although it could do so in an augmented reality arrangement). Instead, its primary purpose in the present embodiments is to allow motion sensing. A technique for using images captured by the camera 322 for motion sensing will be described below in connection with FIG. 10. In these arrangements, the motion detector comprises a camera mounted so as to move with the frame; and an image comparator operable to compare successive images captured by the camera so as to detect inter-image motion.

FIG. 9b makes use of a hardware motion detector 332. This can be mounted anywhere within or on the HMD. Examples of suitable hardware motion detectors are piezo-electric accelerometers or optical fibre gyroscopes. It will of course be appreciated that both hardware motion detection and camera-based motion detection can be used in the same device, in which case one sensing arrangement could be used as a backup when the other one is unavailable, or one sensing arrangement (such as the camera) could provide data for changing the apparent viewpoint of the displayed images, whereas the other (such as an accelerometer) could provide data for image stabilisation.

Figure 10:
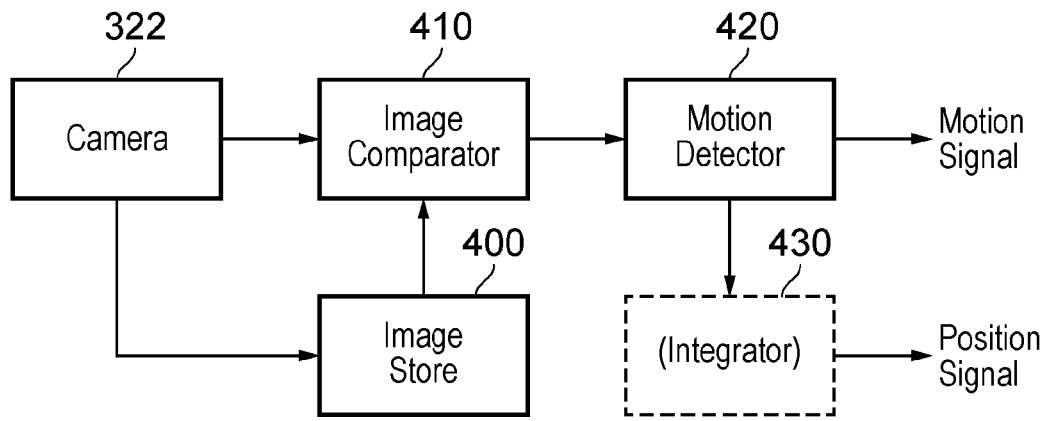
FIG. 10 schematically illustrates a position sensor based on optical flow detection.

FIG. 10 schematically illustrates one example of motion detection using the camera 322 of FIG. 9a.

The camera 322 is a video camera, capturing images at an image capture rate of, for example, 25 images per second. As each image is captured, it is passed to an image store 400 for storage and is also compared, by an image comparator 410, with a preceding image retrieved from the image store. The comparison uses known block matching techniques (so-called "optical flow" detection) to establish whether substantially the whole image has moved since the time at which the preceding image was captured. Localised motion might indicate moving objects within the field of view of the camera 322, but global motion of substantially the whole image would tend to indicate motion of the camera rather than of individual features in the captured scene, and in the present case because the camera is mounted on the HMD, motion of the camera corresponds to motion of the HMD and in turn to motion of the user's head.

The displacement between one image and the next, as detected by the image comparator 410, is converted to a signal indicative of motion by a motion detector 420. If required, the motion signal is converted by to a position signal by an integrator 430.

As mentioned above, as an alternative to, or in addition to, the detection of motion by detecting inter-image motion between images captured by a video camera associated with the HMD, the HMD can detect head motion using a mechanical or solid state detector 332 such as an accelerometer. This can in fact give a faster response in respect of the indication of motion, given that the response time of the video-based system is at best the reciprocal of the image capture rate. In some instances, therefore, the detector 332 can be better suited for use with higher frequency motion detection. However, in other instances, for example if a high image rate camera is used (such as a 200 Hz capture rate camera), a camera-based system may be more appropriate. In terms of FIG. 10, the detector 332 could take the place of the camera 322, the image store 400 and the comparator 410, so as to provide an input directly to the motion detector 420. Or the detector 332 could take the place of the motion detector 420 as well, directly providing an output signal indicative of physical motion.

Other position or motion detecting techniques are of course possible. For example, a mechanical arrangement by which the HMD is linked by a moveable pantograph arm to a fixed point (for example, on a data processing device or on a piece of furniture) may be used, with position and orientation sensors detecting changes in the deflection of the pantograph arm. In other embodiments, a system of one or more transmitters and receivers, mounted on the HMD and on a fixed point, can be used to allow detection of the position and orientation of the HMD by triangulation techniques. For example, the HMD could carry one or more directional transmitters, and an array of receivers associated with known or fixed points could detect the relative signals from the one or more transmitters. Or the transmitters could be fixed and the receivers could be on the HMD. Examples of transmitters and receivers include infra-red transducers, ultrasonic transducers and radio frequency transducers. The radio frequency transducers could have a dual purpose, in that they could also form part of a radio frequency data link to and/or from the HMD, such as a Bluetooth® link.

Figure 11:
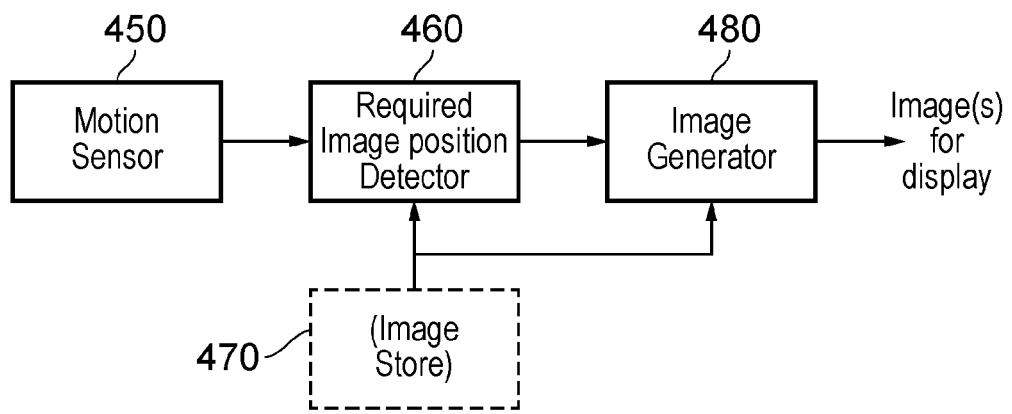
FIG. 11 schematically illustrates image processing carried out in response to a detected position or change in position of an HMD.

FIG. 11 schematically illustrates image processing carried out in response to a detected position or change in position of the HMD.

As mentioned above in connection with FIG. 10, in some applications such as virtual reality and augmented reality arrangements, the apparent viewpoint of the video being displayed to the user of the HMD is changed in response to a change in actual position or orientation of the user's head.

With reference to FIG. 11, this is achieved by a motion sensor 450 (such as the arrangement of FIG. 10 and/or the motion detector 332 of FIG. 9b) supplying data indicative of motion and/or current position to a required image position detector 460, which translates the actual position of the HMD into data defining the required image for display. An image generator 480 accesses image data stored in an image store 470 if required, and generates the required images from the appropriate viewpoint for display by the HMD. The external video signal source can provide the functionality of the image generator 480 and act as a controller to compensate for the lower frequency component of motion of the observer's head by changing the viewpoint of the displayed image so as to move the displayed image in the opposite direction to that of the detected motion so as to change the apparent viewpoint of the observer in the direction of the detected motion.

The operations to be discussed below relate to apparatus and methods for assisting a user wearing an HMD when determining that the user may be in a pathological state. A wide range of users having different ages and varying medical histories may wear the HMD in order to view displayed content and listen to provided audio. Some users may suffer from a long term medical condition such as coronary heart disease, epilepsy, asthma, or diabetes which can cause the user's body to function pathologically and/or may cause an alteration of the user's state of consciousness. Alternatively or in addition, some users may be intoxicated due to the consumption of medication or alcohol which may increase the likelihood of the user entering a pathological state or may contribute to an alteration of the user's state of consciousness.

In Europe, coronary heart disease is the single most common cause of death before 65 and accounts for approximately 16% of male and 10% of female deaths in this age range. In the United Kingdom, it is estimated that every 7 minutes someone will have a heart attack, and every 12 minutes someone will have a stroke. There are over 1.6 million men and over 1 million women currently in the United Kingdom that are believed to have coronary heart disease (source: British Heart Foundation). Epilepsy is another pathological condition which can cause recurrent seizures, and it is estimated that 600,000 people in the United Kingdom suffer from epilepsy. Therefore as a matter of chance, there is a real risk that a person may experience a heart attack, a stroke, a seizure, or another type of medical emergency due to a pre-existing medical condition, during a period of time when an HMD is worn. As such, there is a need for a method and an apparatus which can determine when a user is sufficiently likely to be in a pathological state to trigger one or more processes to provide assistance to the user.

Figure 12:
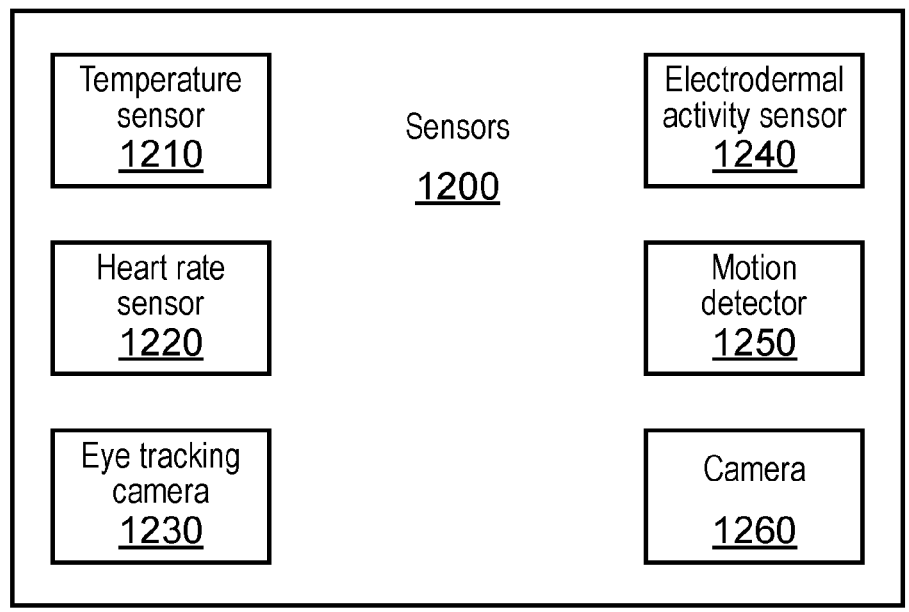
FIG. 12 schematically illustrates a functional block diagram of hardware to detect parameters indicating current properties of a user.

FIG. 12 illustrates a functional block diagram of hardware to detect parameters indicating a user's current properties. In embodiments of the disclosure, one or more sensors 1200 can be provided for detecting one or more parameters indicating one or more current properties of the user wearing the HMD, the one or more sensors comprising one or more from the list consisting of: a temperature sensor 1210; a heart rate sensor 1220; an eye tracking camera 1230; an electrodermal activity sensor 1240; a motion detector 1250; and a camera 1260.

For example, the temperature sensor 1210 may be an infrared thermometer configured to detect infrared radiation emitted from a portion of the user's body such as the user's ear 70 (e.g. eardrum) or the user's forehead. The infrared thermometer may comprise a lens to focus infrared radiation from a portion of the user's body onto an infrared radiation sensor and an electrical signal can be generated by the sensor indicative of the temperature of the portion of the user's body. The temperature sensor 1210 can be configured to detect the infrared radiation emitted from the user's body either when in contact with the user's body or when not in direct contact with the user's body. The temperature sensor 1210 may be provided as part of the HMD and positioned on a portion of the HMD proximate (when being worn) to the user's forehead or either side of the user's forehead (temporal temperature measurement), or may be provided as part of the associated headphone audio transducers or earpieces 60 of the HMD which are configured to fit into the user's left and right ears 70 for tympanic temperature measurement. As such, the headphone audio transducers or earpieces (e.g. earbuds) 60 of the HMD may comprise one or more temperature sensors 1210 so that a temperature of the user's body can be identified from at least one of the user's ear canals. Alternatively or in addition, the temperature sensor 1210 may be positioned on another portion of the user's body such as the axilla, in which case the temperature sensor 1210 may be provided separate to the HMD and the temperature sensor may transmit data indicative of the one or more detected parameters via a wired or wireless communication such as one using the Bluetooth® protocol.

In embodiments of the disclosure, the HMD comprises one or more temperature sensors 1210 configured to detect one or more parameters indicating the temperature of the user's body. Alternatively or in addition, one or more sensors may be positioned on other respective portions of the user's body, and parameters indicative of the temperature of the user's body can be detected at the respective portions of the user's body. This provides an example of one or more temperature sensors 1210 configured to detect one or more parameters indicating a temperature of the body of the user wearing the HMD. More generally this provides an example of one or more sensors 1200 configured to detect one or more parameters indicating a physiological property of the user wearing the HMD.

In embodiments of the disclosure, one or more heart rate sensors 1220 may be provided either as part of the HMD or separate to the HMD. For example, the heart rate sensor 1220 may be positioned to contact the user's skin so that electrical activity associated with the contraction of the user's heart is detected by the heart rate sensor 1220 and one or more detected parameters provide an indication of the beating rate of the user's heart or a pattern (rhythm) of the beating rate of the user's heart. Alternatively or in addition, the heart rate sensor 1220 may comprise an optical sensor and a plurality of light emitting diodes (LEDs) that emit light of different wavelengths in order to detect one or more parameters indicating the user's heart rate. The different wavelengths refract differently off the blood flowing through the user's body and the optical sensor can detect one or more parameters associated with the refracted wavelengths indicative of the changes in blood flow caused by the beating of the user's heart.

The HMD may comprise one or more heart rate sensors 1220 configured to detect one or more parameters indicating the beating rate of the user's heart and alternatively or in addition, one or more heart rate sensors 1220 may be provided separate to the HMD on respective portions of the user's body such as the arm, wrist or chest. In some examples, the HMD comprises one or more heart rate sensors 1220 positioned proximate to the user's neck (for example, placed on an inside surface of a rear headband of the HMD), temporal artery (side of forehead), or ear canal. The heart rate sensor 1220 may be provided on a front portion of the HMD so that the heart rate sensor is proximate to or in contact with a side portion of the user's forehead proximate to the temporal artery. In some embodiments, two respective heart rate sensors may be positioned on either side of the forehead for respectively detecting parameters indicating the beating rate of the user's heart. Alternatively or in addition, one or more heart rate sensors 1220 may be provided as part of the associated headphone audio transducers or earpieces 60 of the HMD which are configured to fit into the user's left and right ears 70 so that one or more parameters indicating the beating rate of the user's heart can be detected from at least one of the user's ear canals.

Figure 13:
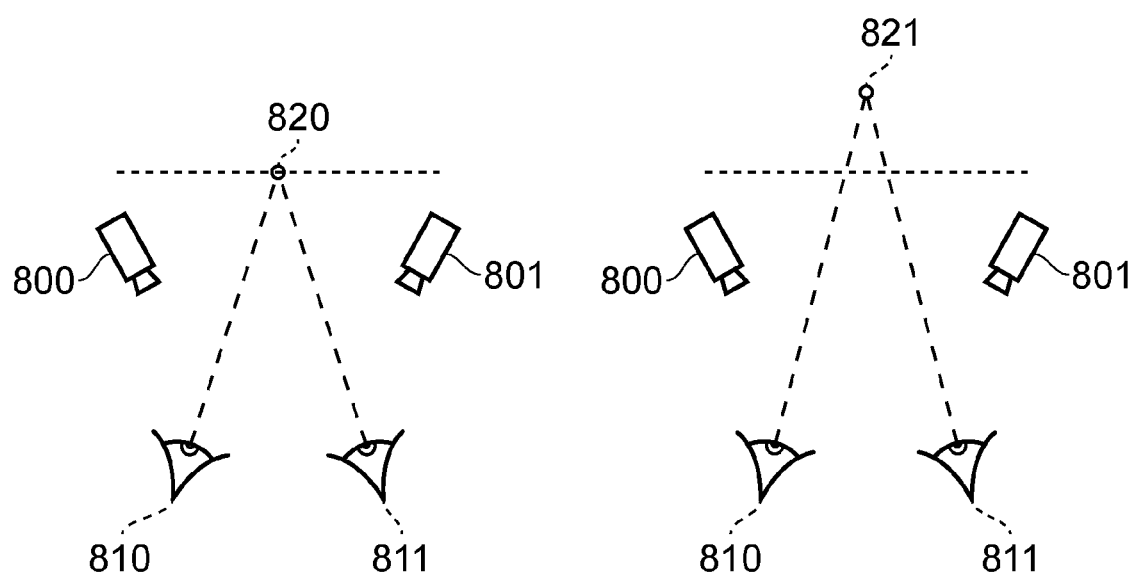
FIG. 13 schematically illustrates two eye tracking cameras used to detect the orientation of the users eyes in an HMD.

In embodiments of the disclosure, the HMD may comprise one or more eye tracking cameras 1230 configured to detect one or more parameters indicating a physical direction in which the eyes are pointing, or in other words, the direction of the user's gaze. For example, the HMD may comprise two respective eye tracking cameras 1230 each configured to detect the orientation of the user's eyes, and one or more infrared or near-infrared light sources. The light source can be used to illuminate at least one of the user's eyes to create reflections of the structure of the eye, and the movement of each eye may be tracked by capturing successive images of the structure of the eye. FIG. 13 shows two eye tracking cameras 800 and 801 that are used to detect the orientation of the eyes 810 and 811 in a head mountable display device. By comparing information about the orientation of each eye 810/811, the so-called vergence of the eyes can be detected. The vergence can then be used to detect where on the display screen 820 (or with respect to a virtual image of a display, as in an HMD) the viewer is looking, and at which apparent depth the viewer is focused on in the case of a 3D image. Alternatively, the orientation of just one of the eyes 810 and 811 can be used to determine a line of sight along which the user eye is focused.

Referring again to FIG. 12, the HMD may comprise two respective eye tracking cameras 1230 to respectively track each eye and detect parameters indicating the direction of the user's gaze and/or the dilation of the user's pupils. The eye tracking cameras 1230 can be configured to capture successive images of the user's eyes and detect one or more parameters indicating the pattern of the user's gaze. For example, the eye tracking cameras 1230 may detect parameters indicating the dilation of each of the user's pupils and the vergence of the user's eyes, which can be associated with a depth of focus of the eye. Variations in the pupil dilation, vergence of the eyes, and the depth of focus of the eyes can be identified from the detected parameters. For example, a sudden change in the pupil dilation, or a pattern of the pupil dilation or a pattern of the direction of the user's gaze, such as a pattern of the vergence of the user's eyes, may be indicative of a change in the user's current state from a non-pathological state to a pathological state.

In embodiments of the disclosure, one or more electrodermal activity sensors 1240 may be provided for detecting one or more parameters indicating the conductance of the user's skin also referred to as electrodermal activity or galvanic skin response. Sweat glands can secrete fluid through pores towards the skin surface and the secreted sweat influences the electrical characteristics of the skin surface such as conductance and resistance. The amount of sweat secreted by the user can be evaluated by providing one or more electrodermal activity sensors 1240 in contact with the user's skin, which detect one or more parameters indicating the electrical properties of the user's skin.

The HMD may comprise one or more electrodermal activity sensors 1240 configured to detect the one or more parameters indicating skin conductance, and alternatively or in addition, one or more electrodermal activity sensors 1240 may be provided separate to the HMD for respective portions of the user's body such as the hands, arms or axilla. For example, the HMD may comprise an electrodermal activity sensor 1240 that detects one or more parameters for identifying the electrical characteristics of a portion of the user's scalp. Alternatively or in addition, the earpieces 60 of the HMD which are configured to fit into the user's left and right ears 70 may comprise one or more electrodermal activity sensors 1240. One or more electrodermal activity sensors 1240 may be built-in to a handheld peripheral that is held by the user when wearing the HMD in order to detect parameters indicating the conductance of the skin on the user's hand.

In embodiments of the disclosure, one or more hardware motion detectors 1250, 332 (as illustrated in FIGS. 9A and 9B) can be mounted anywhere within or on the HMD and can detect one or more parameters indicating one or more from the list consisting of: a motion of the user's head; an average motion of the user's head; an acceleration of the user's head; an orientation of the user's head; a position of the user's head. Examples of suitable hardware motion detectors are piezoelectric accelerometers or optical fibre gyroscopes. Alternatively or in addition, one or more motion detectors 1250, 332 can be provided separate to the HMD for respective portions of the user's body such as the user's arms, legs or chest, and the motion detectors 1250, 332 are configured to detect one or more parameters indicating one or more from the list consisting of: a motion of the user's body; an average motion of the user's body; an acceleration of the user's body; an orientation of the user's body; and a position of the user's body.

Alternatively or in addition, camera-based motion detection can be implemented by providing the camera 1260, 322 mounted on at least one of the HMD or on the games console 300, and the technique of using images captured by the camera for motion sensing, as described previously with reference to FIG. 10, can be implemented. This means that one or more cameras can be mounted on the HMD or the games console 300 or both, and the one or more cameras are configured to detect one or more parameters indicating one or more current properties from the list consisting of: the motion of the user's head; the average motion of the user's head; the acceleration of the user's head; the orientation of the user's head; the position of the user's head; the motion of the user's body; the average motion of the user's body; the acceleration of the user's body; the orientation of the user's body; and the position of the user's body.

One or more parameters indicating the motion of the user's body or the motion of the user's head can be suitably detected by the one or more motion detectors 1250, 332 and/or the one or more cameras 1260, 322. An average of one or more of the detected parameters over a predetermined period of time can provide an indication of the average motion of the user's body or the average motion of the user's head for a predetermined time period. For example, a motion detector 1250 provided as part of the HMD can detect one or more parameters indicating the motion and/or current position of the user's head at a given time, and an average of the one or more parameters over a predetermined period of time can provide an indication of the average motion of the user's head for the period of time. One or more of the parameters detected by the motion detector 1250 may be averaged over a time period (such as 1, 5, or 10 minutes, for example) thus providing an indication of the average motion of the user's head, and the period of time over which one or more parameters are averaged may be suitably adjusted according to the user's preferences. Alternatively or in addition, one or more parameters that indicate the motion of the user's head may be detected by the one or more cameras 1260, 322 and the one or more parameters may be averaged over a predetermined period of time so as to provide an indication of the user's average head motion using camera based motion detection. It will be appreciated that an indication of the average motion of the user's head may be obtained by averaging one or more parameters detected by at least one of a motion detector 1250 provided as part of the HMD and one or more cameras 1260, 322 either provided as part of the HMD or separate to the HMD.

One or more motion detectors 1250, 332 can be provided separate to the HMD for respective portions of the user's body and one or more of the parameters detected by the one or more motion detectors can be averaged over a predetermined period of time. For example, one or more motion sensors may be provided on a user's leg (or both legs) and one or more parameters indicating the motion of the user's leg can be averaged over a predetermined period of time thus providing an indication of the average motion of the user's leg (or both legs) over the predetermined period of time. Similarly, one or more motion detectors may be provided for other portions of the user's body (e.g. each arm, the chest) and one or more detected parameters can be averaged for respective portions of the user's body such that an average motion of each arm may identified or an average motion of the user's chest may be identified. A repeating or oscillating motion of the user's chest may be used to provide an indication of the user's respiratory rate (e.g. number of breaths per minute). The average motion of the user's body may either represent an average motion for a portion of the user's body or may be obtained by combining the average motion for the respective portions of the user's body so that the average leg motion, the average arm motion and the average chest motion, for example, may be averaged to provide an indication of the average motion of the user's body. Alternatively or in addition, one or more cameras 1260, 322 may detect one or more parameters indicating motion of respective portions of the user's body and one or more of the parameters may be averaged over a given time period to provide an indication of the average motion of the portion of the user's body or to provide an indication of the average motion of the user's body.

The one or more sensors 1200 provided as part of the HMD or separate to the HMD can communicate data indicative of the detected parameters to at least one of the HMD, the games console 300 or another device via a wired (physical cable) or a wireless communication link, and processing associated with the one or more parameters can be carried out at either the HMD or the games console 300, or both the HMD and games console 300, or another device. Alternatively or in addition, parameters from the one or more sensors may be at least partially processed by the HMD 20 and/or may be at least partially processed by the games console 300. It will be appreciated that any of the sensors (1210, 1220, 1230, 1240, 1250 and 1260) described can be configured to communicate data indicative of the one or more detected parameters to the HMD or the games console 300 or both via a wired or a wireless communication link, and parameters from the one or more sensors may be at least partially processed at the HMD 20 and/or may be at least partially processed at the games console 300.

Figure 14:
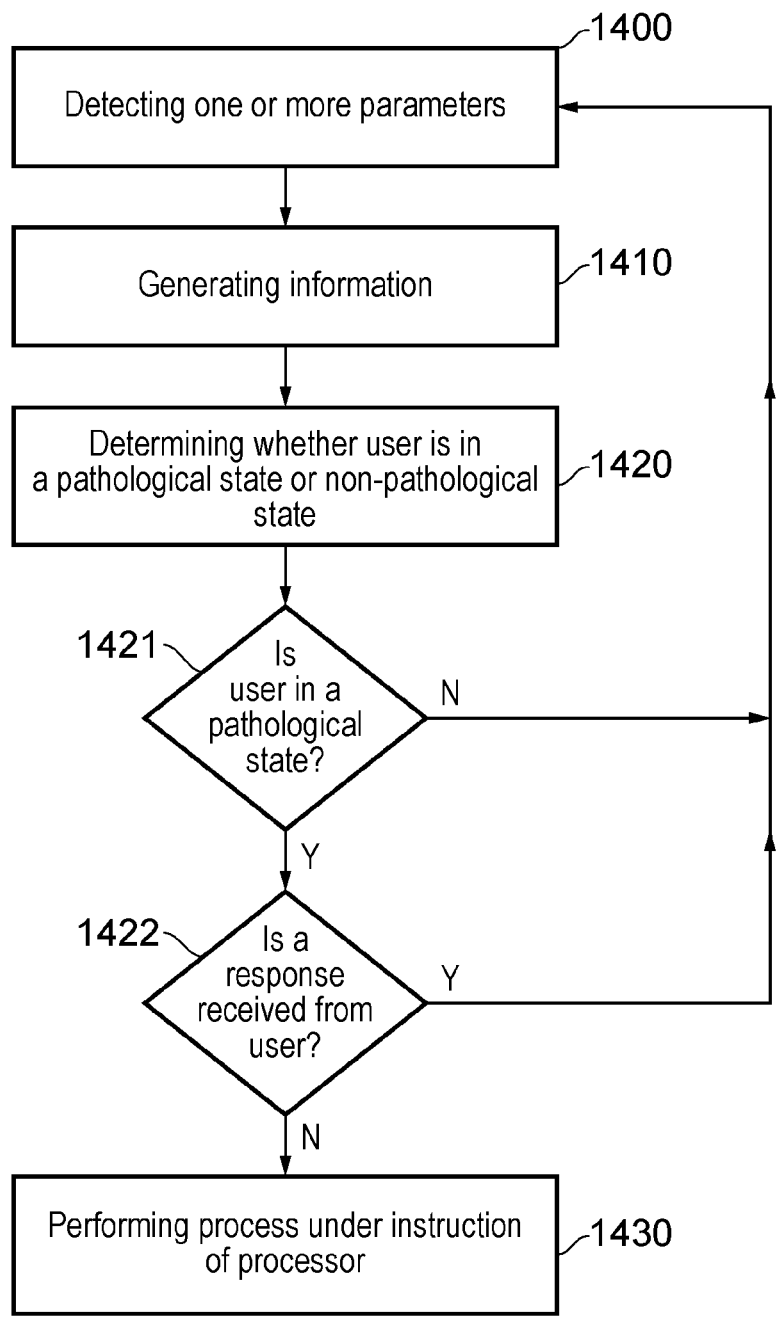
FIG. 14 is a schematic flow chart of a method of assisting a user wearing an HMD when determining that the user may be in a pathological state.

Referring to FIG. 14, there is provided a schematic flow chart in respect of a method of assisting a user wearing an HMD when determining that the user may be in a pathological state, the method comprising the steps of:

detecting (at a step 1400), by one or more sensors, one or more parameters indicating one or more current properties of the user;

generating information (at a step 1410) indicating the one or more current properties of the user based on the one or more parameters;

determining (at a step 1420) whether the user may be in a pathological state or a non-pathological state based on the information indicating one or more of the current properties of the user; and performing (at a step 1430) a process under instruction of a processor in response to determining that the user may be in a pathological state, the process comprising one or more operations that the user can voluntarily instruct when the user is in a non-pathological state.

The one or more sensors 1200 may comprise any combination of the sensors 1210, 1220, 1230, 1240, 1250, 1260 which can be suitably mounted anywhere within or on the HMD or provided separate to the HMD. Each sensor can be configured to communicate data indicative of the one or more detected parameters to at least one of the HMD, the games console 300, the intermediate device 350 and another device comprising a CPU. It will be appreciated that the step 1410 of generating information indicating the one or more current properties of the user can be performed, based on one or more detected parameters, by any of the HMD, the games console 300, the intermediate device 350, the one or more sensors, or another device comprising a CPU, and processing tasks can be shared amongst respective devices.

The generated information indicating the one or more current properties of the user can be communicated either via a wired or wireless communication link between respective devices in order to share the generated information amongst the respective devices.

In some examples, the HMD may comprise one or more sensors in which case the HMD and its one or more sensors may be responsible for detecting (step 1400) the one or more parameters, generating the information (step 1410) indicating the one or more current properties of the user, determining (step 1420) whether the user may be in a pathological state or a non-pathological state based on the information indicating one or more current properties of the user, and performing (step 1430) a process under instruction of a processor in response to determining that the user's body may be in a pathological state, in which the processor is provided as part of the HMD. Alternatively or in addition, some or all of the one or more sensors may communicate data indicative of the one or more detected parameters to the games console 300, the intermediate device 350 or another device comprising a CPU, and the step of generating information may be performed by the games console 300 or the intermediate device 350 or another device. Some or all of the one or more sensors may be provided separate to the HMD and the one or more sensors can be configured to communicate data indicative of the one or more detected parameters to at least one of the HMD, the games console 300, the intermediate device 350 or another device comprising a CPU, and the step 1410 of generating information can be performed by any device receiving the data indicative of the one or more parameters.

Data indicative of the generated information indicating the one or more current properties of the user may be communicated to or from the HMD 20, the games console 300, the intermediate device 350 or any other respective device comprising a CPU. The step 1420 of determining whether the user may be in a pathological state or a non-pathological state based on the information indicating one or more current properties of the user can be performed by any of the HMD 20, the games console 300, the intermediate device 350, another device comprising a CPU or a combination thereof. The step 1420 may determine that the user is in a non-pathological state (see step 1421 in FIG. 14) in which case the method returns to step 1400, and the steps of detecting one or more parameters (step 1400), generating information (step 1410) and determining whether the user may be in a pathological state (step 1420) can be repeated. When it is determined that the user may be in a pathological state (see step 1421 in FIG. 14), the method may optionally comprise a step 1422 where a response is requested from the user within a predetermined period of time or the method may proceed directly to the step 1430 in order to perform a process under instruction of a processor, in dependence upon the properties of the determined pathological state. For example, if the information generated at step 1410 indicates that the position and/or orientation of the user's body and/or the user's head suddenly changes indicating that the user has fallen over, then it may be determined at step 1420 that the user may be in a pathological state such that the method proceeds directly to step 1430 where a process is performed under instruction of a processor in response to determining that the user is in the pathological state. Alternatively, if the generated information indicates that the user is in an altered state of consciousness (in which the user's normal capacity may be inhibited) then a response may be requested from the user (at step 1422) and if a response is received within a predetermined period of time then the method can return to the step 1400 and one or more parameters can be detected. When it is determined that the user may be in a pathological state and no response is received from the user within the predetermined period of time, the method proceeds to the step 1430 and a process can be performed under instruction of a processor, in which the process comprises one or more operations that the user is capable of voluntarily instructing when the user is not in a pathological state.

One or more parameters indicating one or more physiological and/or psychological properties of the user can be detected by the one or more sensors 1200 and used to determine whether the user may be in a pathological state or a non-pathological state. A pathological state may be caused by a medical condition (such as heart disease, epilepsy, or diabetes) that can affect the user's health and limit the user's ability to perform certain functions that they can normally perform when in a non-pathological state. Examples of pathological states include: a heart attack; a stroke; a non-epileptic seizure; an epileptic seizure; an asthma attack; syncope; a panic attack; and an altered state of consciousness. An altered state of consciousness may be characterised by a temporary change in a person's normal mental state without the person being considered unconscious. For example, an altered state of consciousness may occur due to a change in brain function that can be caused by an epileptic event, insufficient blood flow to the brain, or a metabolic disorder such as diabetes mellitus. One or more parameters indicating one or more current properties of the user wearing the HMD can be detected by any combination of the one or more sensors 1200, and information indicating one or more of the current properties of the user can be generated by any of the HMD 20, the games console 300, and the intermediate device 350 based on one or more of the detected parameters. The generated information can be used to determine whether the one or more current properties of the user indicate whether the user may be in a pathological state or a non-pathological state.

Figure 15:
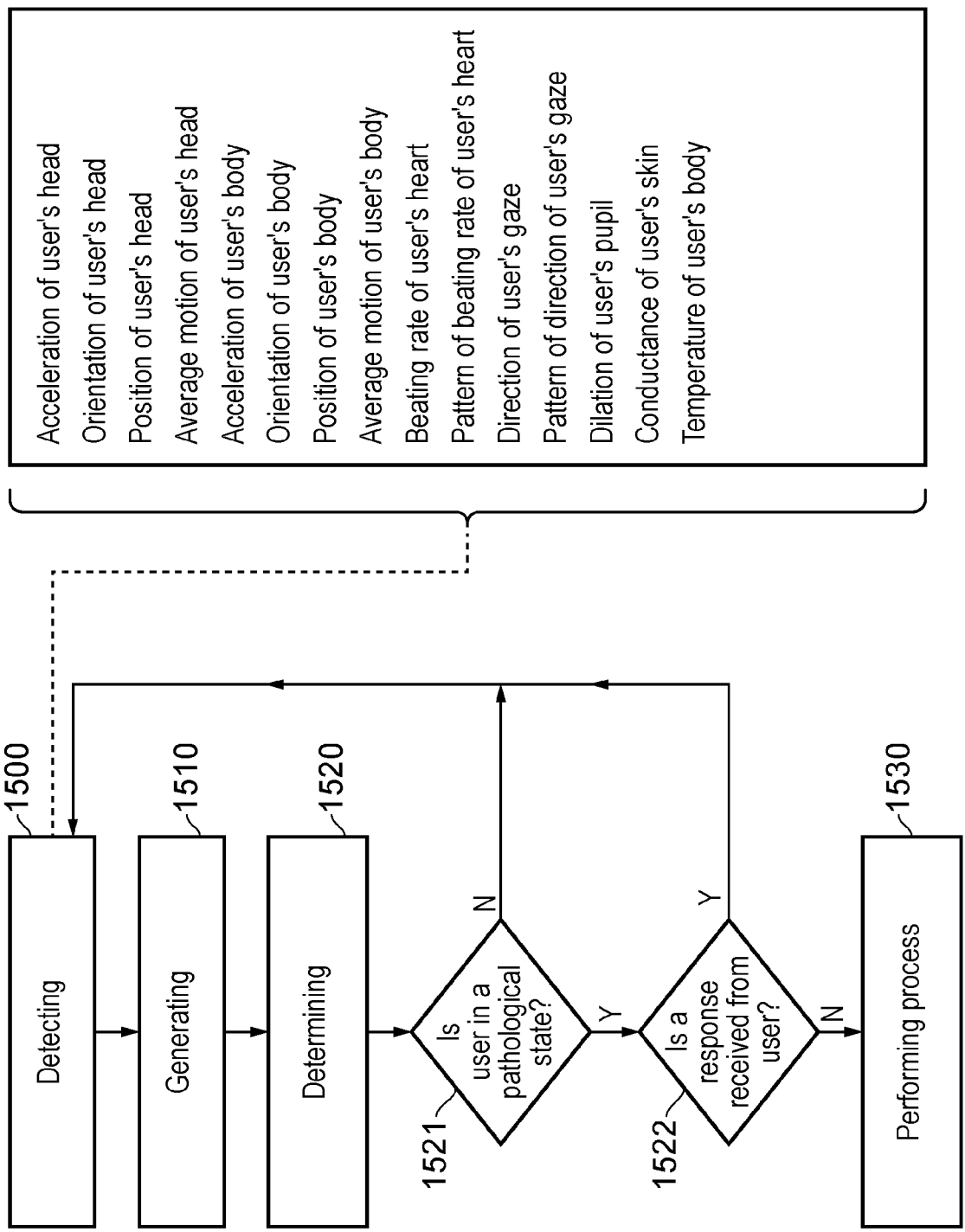
FIG. 15 is schematic flowchart illustrating a method of assisting a user wearing an HMD when determining that the user may be in a pathological state.

FIG. 15 is a schematic flowchart illustrating current properties of a user and a method of assisting a user wearing an HMD when determining that the user may be in a pathological state. At a step 1500 the one or more sensors detect one or more parameters indicating one or more current properties (e.g. physiological properties, properties associated with user motion) of the user comprising one or more from the list consisting of: an acceleration of the user's head; an orientation of the user's head; a position of the user's head; a motion of the user's head; an average motion of the user's head; an acceleration of the user's body; an orientation of the user's body; a position of the user's body; a motion of the user's body; an average motion of the user's body; a beating rate of the user's heart; a pattern of the beating rate of the user's heart; a direction of the user's gaze; a pattern of the direction of the user's gaze; a dilation of at least one of the user's pupils; a conductance of the user's skin; and a temperature of the user's body. At a step 1510 the information indicating the one or more current properties of the user can be generated based on the one or more detected parameters. At a step 1520 it can be determined whether the user may be in a pathological state or a non-pathological state based on the generated information indicating one or more of the current properties of the user. When determining that the user's body may be in a pathological state (step 1520 and step 1521) and when no response is received from the user (step 1522) within a predetermined period of time, a process can be performed at step 1530 under instruction of a processor. The process comprises one or more operations that can typically be instructed by the user when the user is in a non-pathological state, and the one or more operations can be performed under the instruction of the processor in order to assist the user wearing the HMD 20 when the user may be in a pathological state.

In some examples, at the step 1522 a query can be communicated to the user requesting a response from the user within a predetermined period of time, and the user may be notified of period of time within which they are required to respond before the method proceeds to the step 1530. Alternatively or in addition, the step 1522 may comprise a communicating a plurality of queries to the user where a first query requests a response from the user within a first predetermined time period and if no response is received, a second query may be communicated requesting a response within a second time period, and if no response is received from the user after the second time period then the method can proceed to the step 1530.

Figure 16A:
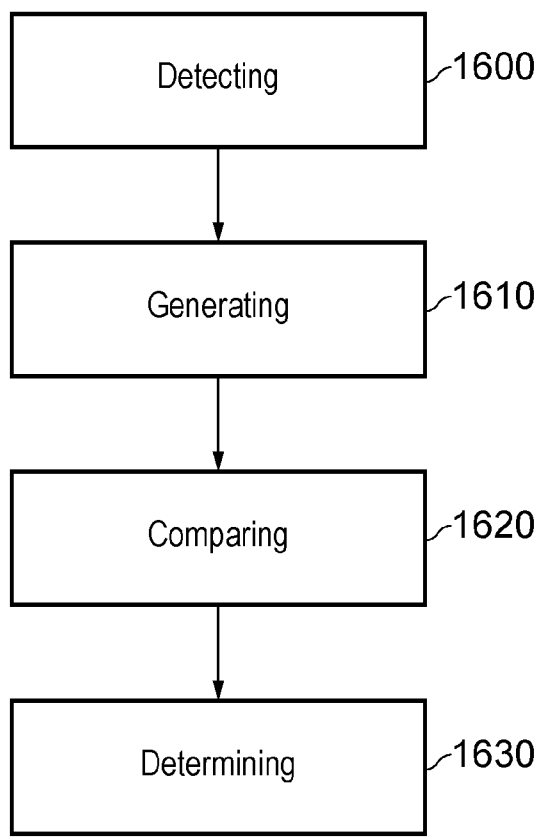
FIGS. 16a and 16b are schematic flowcharts each illustrating a method of determining whether the user may be in a pathological state.

FIG. 16*a* is a schematic flowchart illustrating a method of determining whether the user may be in a pathological state based on a comparison of one or more of the current properties of the user with one or more reference values associated with one or more of the properties, the method comprising:

detecting (at a step 1600), by one or more sensors, one or more parameters indicating one or more current properties of the user;

generating information (at a step 1610) indicating the one or more current properties of the user based on the one or more parameters;

comparing (at a step 1620) one or more of the current properties of the user with one or more reference values associated with one or more of the properties; and determining (at a step 1630) whether the user may be in a pathological state or a non-pathological state based on one or more of the current properties of the user.

Figure 16B:
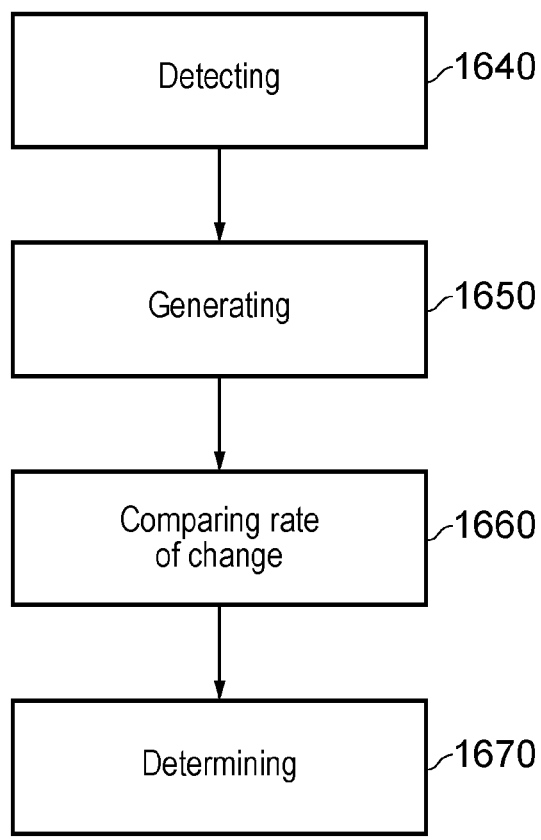

FIG. 16*b* is a schematic flowchart illustrating a method of determining whether the user may be in a pathological state based on a comparison of a rate of change of one or more of the current properties of the user with one or more rate of change reference properties, the method comprising:

detecting (at a step 1640), by one or more sensors, one or more parameters indicating one or more current properties of the user;

generating information (at a step 1650) indicating the one or more current properties of the user based on the one or more parameters;

comparing (at a step 1660) a rate of change of one or more of the current properties of the user with one or more rate of change reference values associated with one or more of the properties; and determining (at a step 1670) whether the user may be in a pathological state or a non-pathological state based on the rate of change of one or more of the current properties of the user.

Information indicating the one or more current properties of the user can be generated based on the one or more parameters, and the information can be used in order to compare one or more of the current properties of the user with the one or more reference values associated with one or more of the properties. The information indicating the one or more current properties of the user can be communicated to any of the HMD 20, the games console 300 and the intermediate device 350, and the step 1660 of comparing can be performed by any of the HMD, the games console and the intermediate device. Processing tasks associated with comparison of one or more current properties with one or more reference values (step 1620) and one or more rate of change reference values (step 1660) may be shared amongst the respective devices 20, 300, 350.

At least one reference value may be provided for each property of the user that is illustrated in FIG. 15. For example, a first reference value may be associated with the beating rate of the user's heart, a second reference value may be associated with the pattern of the beating rate of the user's heart, and a third reference value may be associated with the temperature of the user's body. In this case, using the information indicating the one or more current properties, a current property of the user such as the beating rate of the user's heart may be compared with the first reference value so as to determine whether the user's heart rate is higher or lower than normally expected and the magnitude by which the user's current heart rate differs from the normally expected heart rate for the user. Similarly, the information may be used to compare the pattern of the beating rate of the user's heart with the second reference value to determine whether the current pattern of the beating rate of the user's heart is substantially the same as normally expected (regular rhythm) or whether it is not substantially the same as normally expected (irregular rhythm). As such, the one or more current properties of the user may be compared with one or more reference values representing typical (normal) properties expected for when the user is in a non-pathological state, and differences between the one or more current properties and one or more non-pathological reference values can indicate whether the user may be in a pathological state or a non-pathological state. For example, a pathological state such as a heart attack may be characterised by an irregular rhythm of the beating rate of the heart. As such, the pattern (rhythm) of the heart's beating rate detected by the heart rate sensor 1220 may be compared with a regular pattern (non-pathological reference value) for the beating rate expected when the user is in a non-pathological state to determine if the user may be in a pathological state or a non-pathological state.

Alternatively or in addition, a first reference value and a second reference value may be associated with each property of the user that is illustrated in FIG. 15. For example, at least a first reference value and a second reference value may be associated with the beating rate of the user's heart, at least a third reference value and a fourth reference value may be associated with the pattern of the beating rate of the user's heart, and at least a fifth reference value and a sixth reference value may be associated with the temperature of the user's body. In this case, the information indicating the one or more current properties of the user can be used to compare a current property of the user, such as the beating rate of the user's heart, with two or more reference values to determine whether the beating rate of the user's heart is within a range defined by the first reference value and the second reference value or whether the beating rate of the user's heart is outside this range. For example, a first reference value associated with the beating rate of the user's heart may be set to 110 beats per minute, and a second reference value associated with the beating rate of the user's heart may be set to 50 beats per minute, and it can be determined whether the user's heart rate does or does not occupy a value within this range based on the comparison. It will be appreciated that any suitable number of reference values can be associated with a given property of the user and each current property of the user can be compared with a plurality of reference values.

Alternatively or in addition, the one or more current properties of the user may be compared with one or more reference values associated with properties exhibited when a person may be in a pathological state. The one or more current properties of the user may be compared with one or more reference values associated with properties that are expected to be exhibited by a person when in a specific pathological state (pathological reference value). For example, a pathological state such as an epileptic seizure may be characterised by certain properties such as lip-smacking, convulsions, or rolling of the eyes. A reference value can be provided that is associated with rolling of the eyes, or lip-smacking, or convulsions of portions of the body, for example. As such, a pathological reference value associated with a property that is exhibited when a person may be in a pathological state can be compared with one or more current properties of the user to determine whether the user is exhibiting properties that commonly occur when a person may be in a pathological state.

For example, a pathological state such as a heart attack or a stroke may be identified by a sudden increase or decrease of the beating rate of the user's heart and an irregular pattern of the heart rate (abnormal heart rhythm). In addition, during a heart attack or a stroke a person may secrete a larger amount of sweat from their sweat glands thus altering the conductivity of their skin. By detecting one or more parameters indicating at least the beating rate of the user's heart (using one or more heart rate sensors 1220), the pattern (rhythm) of the beating rate of the user's heart, and optionally the conductance of the user's skin (using one or more electrodermal activity sensors 1240) and comparing one or more of these current properties with one or more reference values (associated with properties characteristic of a non-pathological state and/or reference values associated with properties characteristic of a specific pathological state such as a heart attack or stroke), it is possible to determine whether or not the user may be in a pathological state corresponding to a heart attack or a stroke.

Epilepsy is a group of neurological disorders in which electrical activity in the brain can cause the user to experience seizures. Non-epileptic seizures can occur which are not caused by electrical activity in the brain, but instead may be caused by psychological conditions such as mental health problems. A pathological state such as a seizure may cause the head and/or portions of the body to shake, breathing difficulty, loss of consciousness, and/or eye rolling for example. It will be appreciated that other properties associated with atonic seizures (falling to the ground), tonic seizures (losing balance, falling to the ground), myoclonic seizures (twitching, jerking), absence seizures (eye fluttering, loss of awareness) and tonic-clonic seizures may similarly be considered, and one or more parameters indicating any of these current properties can be detected using a combination of sensors 1200. For example, one or more eye tracking cameras 1230 can be configured to detect one or more parameters indicating the direction of the user's gaze and/or a pattern of the direction of the user's gaze, and one or more cameras 1260 and motion detectors 1250 can be configured to detect one or more parameters indicating one or more current properties such as the acceleration, orientation, position and/or average motion of the user's head and/or the acceleration, orientation, position and/or average motion of the user's body. Therefore, based on one or more of the current properties and one or more reference values (reference values associated with properties characteristic of a non-pathological state and/or reference values associated with properties characteristic of a specific pathological state) it is possible to determine whether or not the user may be in a pathological state corresponding to a seizure.

Syncope, also known as fainting, is another example of a pathological state in which a temporary reduction in the flow of blood to the brain can cause loss of consciousness or an alteration in the user's state of consciousness, which may cause the user to lose their balance and fall to the ground. One or more of the motion detectors 1250, 332 and/or one or more of the cameras 1260, 322 can be configured to detect one or more parameters indicating at least one of the acceleration, orientation, position and average motion of the user's head and/or the user's body, and information indicating such properties can be compared with one or more reference values to determine whether the user may have fallen to the ground and may be in a pathological state. For example, a reference value associated with the average motion of the user's body or head may be set depending on previously detected parameters or may be set depending on the type of content to be presented to the user wearing the HMD (e.g. type of game). Alternatively or in addition, a predetermined criterion may be satisfied which indicates that the user may be in a pathological state. For example, a predetermined criterion may be satisfied if the one or more cameras 1260, 322 detect a position of the user's head indicating that the user's head is in contact with or within a predetermined distance (e.g. 10 cm) of the floor for a predetermined period of time, which may indicate that the user has fallen to the ground. Alternatively or in addition, the one or more motion detectors 1250, 332 and/or the one or more cameras 1260, 322 may detect one or more parameters indicating that the user has fallen to the ground and a predetermined criterion may be satisfied if the user's body remains in such a position and/or orientation for a predetermined period of time.

Asthma is a condition which can affect a person's breathing capabilities when the airways responsible for carrying air to and from the lungs become narrower due tightening of the muscles or inflammation of the airway lining. The onset of an asthma attack may mean that the user struggles to breathe properly such that, in an attempt to provide more oxygen to the lungs, the user's respiratory rate increases. An asthma attack may thus be characterised by a sudden change in the user's respiratory rate which may be identified based on one or more parameters detected by one or more of the motion detectors 1250, 332 indicating the repeating or oscillating motion of the user's chest. As such, information indicating the motion of the user's chest may be used to determine the user's respiratory rate and whether or not it exceeds one or more reference values associated with the user's respiratory rate, or whether the rate of change of the user's respiratory rate indicated by the motion of the user's chest exceeds a corresponding rate of change reference value, which may indicate that the user may be in a pathological state.

A panic attack may similarly be characterised by properties such as shortness of breath as well as heart palpitations and/or sweating. Shortness of breath may cause the user's respiratory rate to increase suddenly which can be identified based on one or more parameters detected by one or more of the motion detectors 1250, 332. In addition, one or more parameters may be detected indicating the beating rate of the user's heart (using one or more heart rate sensors 1220), the pattern (rhythm) of the beating rate of the user's heart, or the conductance of the user's skin (using one or more electrodermal activity sensors 1240) which can each be compared with one or more reference values to determine whether the user may be in a pathological state or a non-pathological state.

An altered state of consciousness may be caused by a number of pathological conditions such as diabetes, as well as due to pharmacological effects, and may be characterised by a consistent failure of the user's eye to track a point of interest in the images displayed to the user by the HMD. For example, if text is presented to the user, it is possible to predict a sequence of positions that a user's eye would fixate on as the user read the words. Similarly, one may expect a user's eyes to focus on a reticule or other in-game targeting system, for example if it changed colour or intersected with a target, or to regularly look in a rear-view mirror in a racing game, for example if a competitor is close behind. If the user's eyes fail to match this predicted behaviour, it could be indicative of an altered state of consciousness. Hence more generally it will be appreciated that the failure of the user's eye to track a point of interest may not be limited to tracking a moving object (such as an enemy) but also tracking a stationary object such as a reticule (e.g. a wandering gaze rather than locking-on) or a failure to follow a normal self-instigated track through successive points of interest, such as will occur when reading normally. Deviations from a norm that are considered significant enough to indicate a possible pathological state may be detected by use of one or more thresholds, which in turn may be determined empirically.

Hence more generally, the generated information indicating the one or more current properties of the user may be used to determine a likelihood of the user's body being in a pathological state according to a comparison of the information with one or more respective reference values (thresholds). Alternatively or in addition, a likelihood of the user's body being in a pathological state can be determined based on whether or not one or more predetermined criterion are satisfied.

Figure 17:
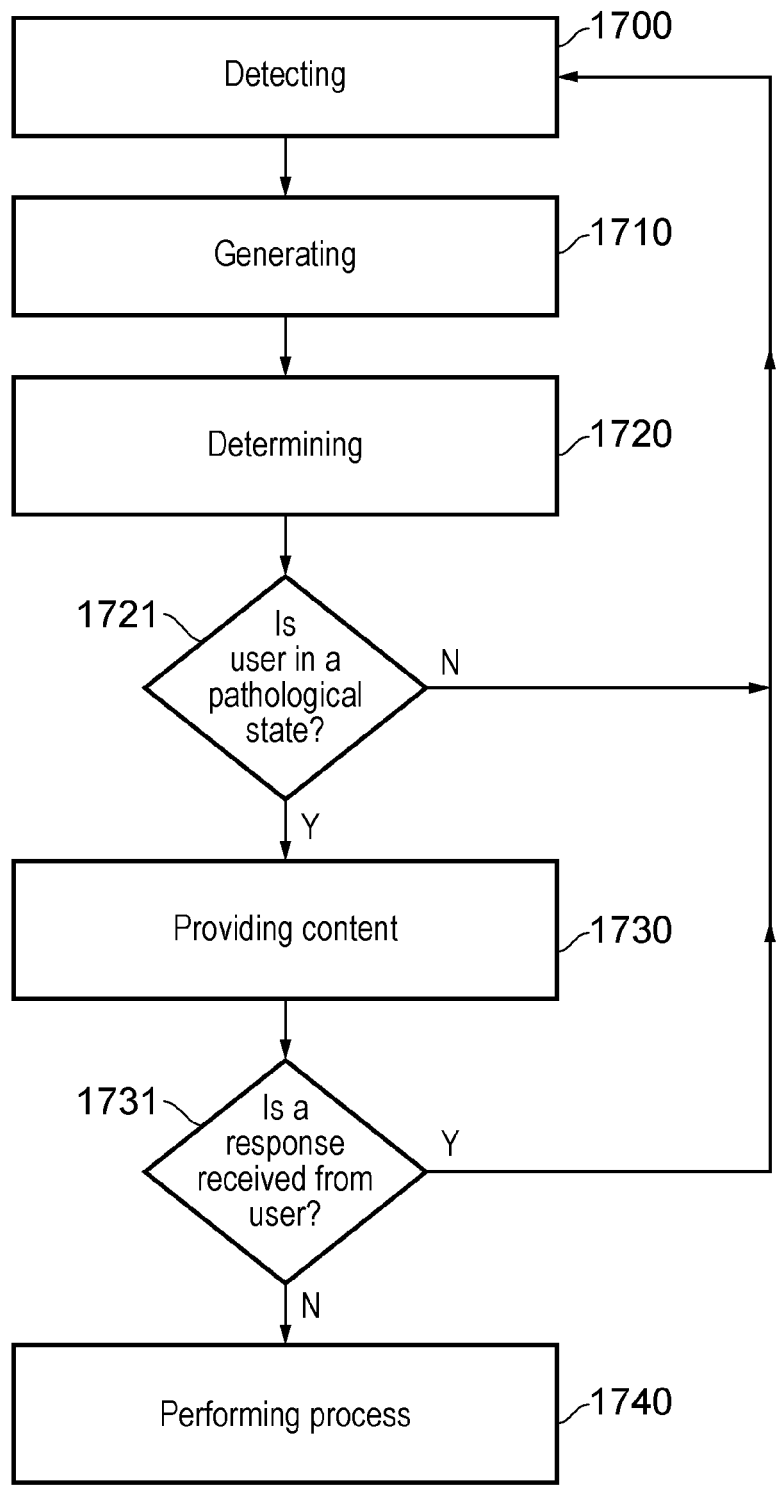
FIG. 17 is a schematic flowchart illustrating a method of determining whether a user may be in a pathological state.

FIG. 17 is a schematic flowchart illustrating a method of determining whether a user may be in a pathological state and providing a content to the user requesting a response within a predetermined period of time, comprising:

detecting (at a step 1700), by one or more sensors, one or more parameters indicating one or more current properties of the user;

generating information (at a step 1710) indicating the one or more current properties of the user based on the one or more parameters;

determining (at a step 1720) whether the user may be in a pathological state or a non-pathological state based on the information indicating one or more of the current properties of the user and when it is determined that the user may be in a pathological state, providing (at a step 1730) a content to the user requesting a response from the user within a predetermined period of time; and performing (at a step 1740) a process under instruction of a processor in response to determining that the user may be in a pathological state and no response is received from the user within the predetermined period of time, the process comprising one or more operations that the user can voluntarily instruct or perform when the user is in a non-pathological state.

The step 1710 of generating the information and the step 1720 of determining whether the user may be in a pathological state or a non-pathological state can be performed by any of the HMD 20, the games console 300 or the intermediate device 350. For example, the step 1710 and the step 1720 may both be performed by the HMD 20, or may both be performed by the games console 300, or the HMD 20 may generate information (step 1710) and the game console 300 may receive the generated information and determine (step 1720) whether the user may be in a pathological state or a non-pathological state. Upon determining that the user may be in a pathological state, a content can be generated and provided (step 1730) to the user wearing the HMD either as audio content provided by the HMD's associated headphone audio transducers or as visual content that can be presented to the user on the display element 150 of the HMD, or both as audio and visual content. As such at the step 1730, at least one of an audio content and a visual content can be provided to the user requesting a response from the user within the predetermined period of time, and if the user does not respond within the predetermined period of time the method may proceed to step 1740 in order to perform a process under instruction of a processor. Alternatively, when no response is received from the user within the predetermined period of time when the first content is provided to the user, a second content may be provided to the user requesting a response from the user that may be the same or may be different to the response requested by the first content. If the user does not respond to the second content within a second predetermined period of time then the method can proceed to the step 1740 and the process can be performed under instruction of the processor.

Hence more generally, a first content can be provided to the user requesting a first response within a first predetermined period of time and if no response is received within the first predetermined period of time then a second content can be provided to the user requesting a second response from the user within a second predetermined period of time. Alternatively or in addition, the first content provided to the user can comprise audio content with a first volume and the second content provided to the user can comprise audio content with a second volume, wherein the second volume is greater than the first volume. Alternatively or in addition, the first content provided to the user can comprise visual content that can be displayed by a first portion of the display element 150 of the HMD 20 and the second content provided to the user can comprise visual content that can be displayed on a second portion of the display element 150 of the HMD 20, wherein the second portion is larger than the first portion. As such, the first visual content may be generated by the processor and provided to the user such that the visual content occupies a smaller portion (e.g. 25%) of the image observed by the user compared to the second visual content which may be generated by the processor and provided to the user such that the visual content occupies a larger portion (e.g. 50%, 75%, 100%) of the image observed by the user.

For example, the processor responsible for generating the image displayed by the HMD may be provided as part of the games console 300 (or as part of the HMD), and the processor can be configured to generate the visual content to be displayed by the HMD so that at least a portion of the image displayed by the HMD comprises information requesting a response from the user when it is determined at step 1720 that the user may be in a pathological state. Alternatively or in addition, the audio content may be provided to the user so that the user hears audio (e.g. a voice) requesting a specific response from the user. In some examples, the content provided to the user may request the user to respond by inputting a specific command to a handheld controller (e.g. the audio and/or visual content may request the user to press a specific button of the handheld controller, or a combination of specific buttons, or a sequence of buttons). Alternatively or in addition, the content provided to the user may request the user to perform a specific gesture or action such as a waving gesture or a thumbs-up gesture which can be identified by one or more of the cameras 1260 or one or more of the motion detectors 1250. Hence more generally, the content provided to the user may request the user to respond by performing a gesture that can be recognised by at least one of a camera and a motion detector in order for the user to indicate that the user does not require assistance.

In some examples, when it is determined that the user may be in a pathological state based on information indicating one or more current properties of the user's eye(s) (based on parameters detected by one or more of the eye tracking cameras 1230) then the content provided to the user may request the user to respond by performing an action with at least one of their eyes. For example, the content may request the user to respond by directing their gaze in a specific direction for a certain period of time or may request the user to blink (or wink) a predetermined number of times within a predetermined period of time. In this case, if the user fails to provide a response to the provided content in accordance with the requested response, then the second content may be provided to the user requesting the user to respond by performing an action with a portion of the body that is not the user's eye(s) (e.g. waving gesture, thumbs-up gesture or press button on handheld controller). Alternatively or in addition, if one or more parameters indicating at least one of a position, an orientation, an acceleration, and an average motion of the user's head are used in determining that the user may be in a pathological state, then the first content provided to the user may request the user to respond by adjusting a property of the user's head in a specific manner (e.g. rotate head 90 degrees to the left or right and/or perform a slow nodding gesture), and if the user fails to provide a suitable response then the second content may be provided to user requesting a response different of the response requested by the first content. Hence more generally, when determining that the user may be in a pathological state, the first content can be provided to the user requesting a first response from a first portion of the user's body and if the user fails to provide a response in accordance with the requested response then the second content can be provided requesting a second response from a second portion of the user's body.

It will be appreciated that the step 1730 of providing a content to the user can be performed using content generated by a processor provided as part of the HMD, the games console 300 or the intermediate device 350. In some examples, the processor responsible for generating the image displayed by the HMD may be provided as part of the games console 300 and the processor provided as part of the HMD may determine that the user may be in a pathological state, in which case the processor provided as part of the HMD 20 may generate a visual content requesting a response from the user and the visual content can be overlaid onto the image generated by the games console 300, such that the visual content at least partially obscures a portion of the image generated by the games console 300.

Figure 18:
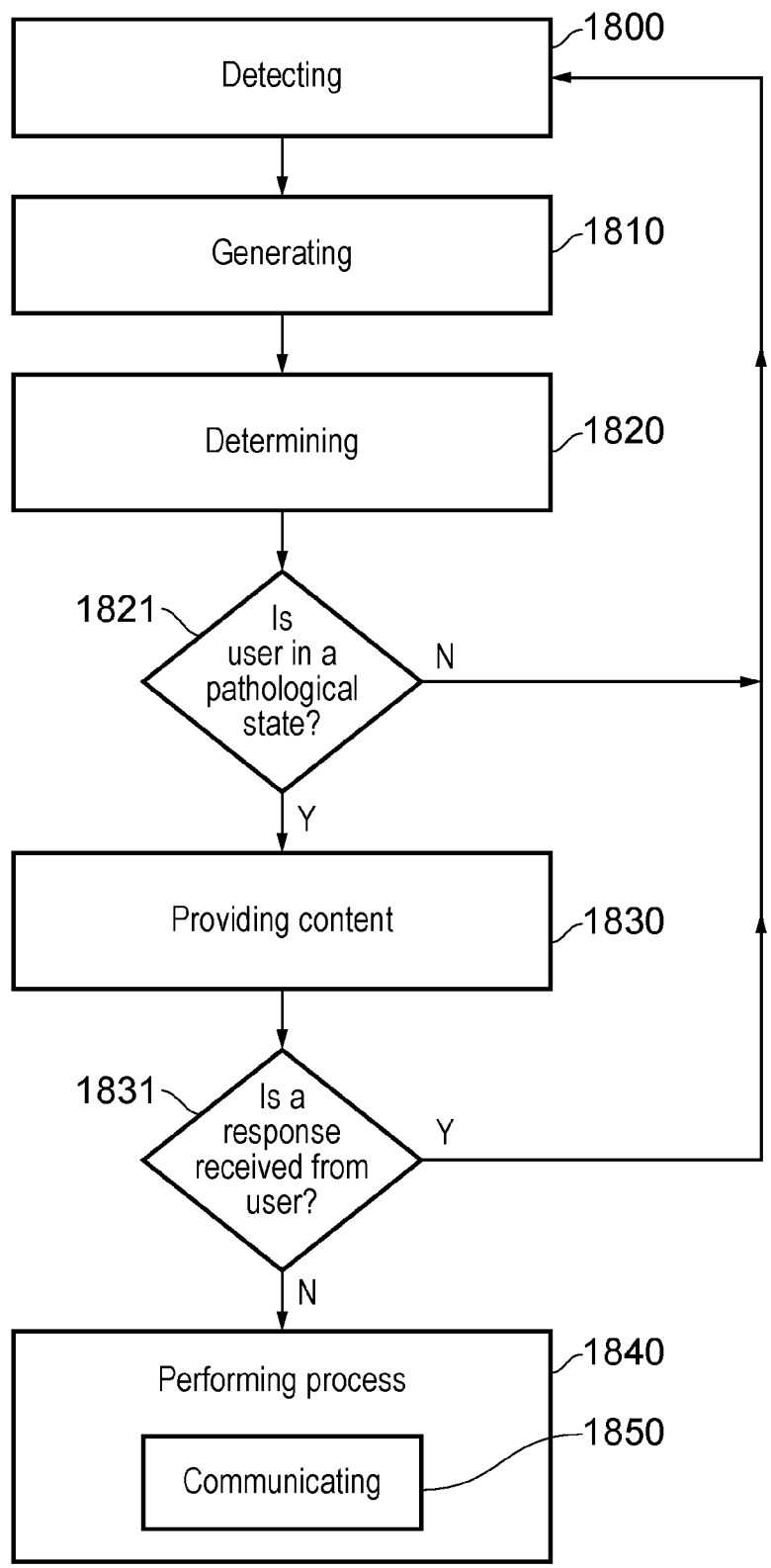
FIG. 18 is a schematic flowchart illustrating a method of assisting a user wearing an HMD.

FIG. 18 is a schematic flowchart illustrating a method of assisting a user wearing an HMD in which a signal can be communicated to a communication device when the user may be in a pathological state, the method comprising:

detecting (at a step 1800), by one or more sensors, one or more parameters indicating one or more current properties of the user;

generating information (at a step 1810) indicating the one or more current properties of the user based on the one or more parameters;

determining (at a step 1820) whether the user may be in a pathological state or a non-pathological state based on the information indicating one or more of the current properties of the user and when it is determined that the user may be in a pathological state, providing (at a step 1830) a content to the user requesting a response from the user within a predetermined period of time; and performing (at a step 1840) a process under instruction of a processor in response to determining that the user may be in a pathological state and no response is received from the user within the predetermined period of time, the process comprising one or more operations that the user can voluntarily instruct or perform when the user is in a non-pathological state, comprising communicating (at a step 1850) a signal to a communication device indicating that the user is experiencing a medical emergency.

Based on the information indicating one or more current properties of the user it may be determined at step 1820 that the user may be in a pathological state. When determining that the user may be in a pathological state (at step 1820 and step 1821), the method may either proceed directly from the step 1820 to the step 1840 in order to perform a process under control of a processor, or may instead proceed from the step 1820 to the step 1830 to provide a content to the user requesting a response from the user within a predetermined period of time and then proceed to the step 1840 if no response is received from the user. Depending on the one or more current properties of the user, the step 1820 may determine that the severity of the pathological state indicates that the user is experiencing a medical emergency such as a heart attack or a stroke, in which case the method may proceed directly from step 1820 to step 1840 so as to perform a process under control of a processor without providing content to the user requesting a response from the user.

Consequently, a method of assisting a user wearing an HMD is provided in which a signal can be communicated to a communication device when the user may be in a pathological state, the method comprising:

detecting (at a step 1800), by one or more sensors, one or more parameters indicating one or more current properties of the user;

generating information (at a step 1810) indicating the one or more current properties of the user based on the one or more parameters;

determining (at a step 1820) whether the user may be in a pathological state or a non-pathological state based on the information indicating one or more of the current properties of the user; and performing (at a step 1840) a process under instruction of a processor in response to determining that the user may be in a pathological state, the process comprising one or more operations that the user can voluntarily instruct when the user is in a non-pathological state, comprising communicating (at a step 1850) a signal to a communication device indicating that the user is experiencing a medical emergency.

As such, depending on the one or more current properties of the user and the severity of the pathological state that the user might be in, the method may or may not proceed directly from step 1820 to step 1840, and step 1830 and step 1831 can be optional depending on the properties of the pathological state. If it is determined at step 1820 that the user may be in a pathological state that is not considered to be a medical emergency, such as a panic attack, then the method may proceed from step 1820 to step 1830 (via step 1821) so as to provide a content to the user requesting a response from the user, and when no response is received from the user within the predetermined period of time the process may be performed under instruction of the processor.

For example, during normal conditions when the user is standing up playing a game, one or more parameters indicating the position of the user's head may be detected which can be used to provide an indication of an average height of the user's head (such as normal head height with respect to the ground the user is standing on) that is expected when the user is standing up. If the one or more detected parameters indicating the position of the user's head indicate that the height of the user's head suddenly changes from the average head height to a head height that is proximate to the floor upon which the user was initially standing on (e.g. head height indicates that the user's head is less than 20 cm from the floor), then the information generated at step 1810 indicating the position of the user's head can be used to determine that the user has fallen over and the user may be in a pathological state. In addition, to detecting a sudden change in the height of the user's head, one or more parameters detected by one or more sensors 1200 may simultaneously indicate that the user may be in a pathological state. For example, the one or more detected parameters may indicate that the user's eyes are rolling backwards, or that the rhythm of the user's heart beat is irregular (other parameters may simultaneously be detected that indicate properties characteristic of other pathological states). As such, it may be determined at step 1820 that the user has fallen over and one or more current properties of the user may be associated with one or more properties characteristic of a specific pathological state. In this case, the current properties of the user may be such that it is determined at step 1820 that the user may be in a pathological state which requires emergency medical assistance, and the method may proceed directly to step 1840 in order to perform a process under instruction of a processor, comprising communicating a signal to a communication device, the signal indicating to the communication device that the user is experiencing a medical emergency.

In embodiments of the disclosure, when detecting at least one of an acceleration of the user's head that is greater than a predetermined threshold indicating an impact with an external object and a position of the user's head indicating the user's head is proximate to an approximately horizontal resting surface, the step of determining comprises the step of:

presenting a content to the user requesting a response from the user within a predetermined period of time. For example, the content may be consistent with the current game (for example, 'Do you want to save the game at this point?' or 'Do you want to start quest X?', which serve to prompt a response from the user without being too intrusive if, in fact, the user is fine. The apparatus may then wait for a predetermined time before deciding that the user is unresponsive. The amount of time may be fixed, or may vary depending on what other indicators of pathology have been detected. Alternatively, or in addition (for example in the absence of a timely response to the first question), a more intrusive presentation may be made, such as pausing the game and switching to a separate UI, and/or asking for a response from the user to confirm that they are well. Such content may be selected to contrast significantly from the previous in-game content, for example in terms of colour palette or distribution (e.g. switching to an all-red background) and/or brightness (e.g. maximising brightness). Any visible presentation may be accompanied by a sound stimulus as well.

As described previously, the step 1840 of performing a process may be performed under instruction of a processor provided as part of the HMD 20, or games console 300 or intermediate device 350, and as such the step 1850 of communicating the signal to the communication device may be performed under instruction of a processor 20, 300, 350. Any of the HMD 20, the games console 300 or the intermediate device 350 can be configured to communicate the signal indicating that the user is experiencing a medical emergency to each other, as well as to another communication device via a wired or wireless communication link. For example, when it is determined that the user is experiencing a medical emergency, either the HMD 20 or the games console 300 may transmit the signal indicating that the user is experiencing a medical emergency via a wired (such as a USB) or a wireless (such as WiFi or Bluetooth) connection to an access point (AP or WAP), and the signal can be communicated to another communication device that may be at a geographical location different to the geographical location of the HMD 20 and the games console 300. For example, a signal indicating that the user is experiencing a medical emergency may be communicated to a communication device of a local emergency service. Alternatively or in addition, the HMD 20 or the games console 300 may communicate the signal to a mobile communication device via a wireless communication and the signal may comprise instructions for instructing the mobile communication device to communicate the signal to another communication device via a cellular network. In some examples, the mobile communication device may be the user's personal mobile communication device and any of the HMD 20, the games console 300, and the intermediate device 350 can communicate the signal to the user's personal mobile communication device instructing the device to contact the emergency services via a cellular or mobile network.

In embodiments of the disclosure, the step 1840 of performing a process under instruction of a processor in response to determining that the user may be in a pathological state, comprises: selecting a communication device from a plurality of communication devices according to in case of emergency contact information; and communicating a signal to a communication device indicating that the user is experiencing a medical emergency. The HMD 20, the games console 300 and/or the intermediate device 350 may store emergency contact information for the user such as a phone number for the emergency services or a phone number of a friend or relative, which can be entered by the user prior to playing a game or viewing a movie. For example, contact information comprising one or more telephone numbers and/or email addresses may be stored under specific names (e.g. "ICE1", "ICE2", "ICEX", or "Emergency Contact") indicating that one or more of these contacts are to be contacted in the case of an emergency. Upon determining that the user may be in a pathological state at step 1820, the method may optionally include step 1830 and proceed to step 1840 when no response is received from the user within the predetermined period of time, or may proceed directly to step 1840. At the step 1840, the processor 20, 300, 350 can access the emergency contact information that is stored for the user and the signal indicating that the user is experiencing a medical emergency can be communicated to a communication device corresponding to the emergency contact information. This means that at least one of the local emergency services or a friend of the user can be informed that the user is experiencing a medical emergency.

In embodiments of the disclosure the process performed under instruction of the processor, comprises one or more operations that the user can voluntarily instruct when the user is in a non-pathological state, wherein the one or more operations comprise one or more from the list consisting of: terminating a content that is currently output by the HMD; outputting an audio signal for alerting another user; and instructing a processing device to transmit at least an image signal comprising an image of the user wearing the HMD to a processing device of another user.

When in a pathological state the user may be prevented from performing certain operations that the user would expect to be able to perform when in a non-pathological state. For example, when in a pathological state the user may be unable to speak coherently and may also be unable to accurately control portions of their body such as their hands, arms and legs. As such, when in a pathological state the user may be unable to correctly enter controller input data or accurately perform specific gestures that can be recognised by a camera or motion detector 1250. This means that the user may be unable to voluntarily exit a game being played, voluntarily stop a movie being output by the HMD, or verbally communicate with another nearby user. Therefore, when determining that the user may be in a pathological state, a processor can instruct the HMD 20 to terminate at least one of an image content and an audio content that is currently output by the HMD as the user may be unable to voluntarily instruct this operation when in a pathological state. Alternatively or in addition, when in a pathological state the user may be unable to verbally communicate with another nearby user also wearing an HMD. For example, another user may be in the same room as the user wearing the HMD but may not be able to see the user when also wearing an HMD. As such, when in a pathological state the user wearing the HMD may attempt to verbally communicate with the other nearby user, but the user may be prevented from speaking coherently or speaking at all. Therefore, when determining that the user may be in a pathological state, a processor can be configured to generate an audio signal and any of the HMD 20, the games console 300 and the intermediate device 350 can be instructed to output the generated audio signal so as to alert another nearby user that the user wearing the HMD 20 may be in a pathological state. For example, the HMD 20 may be instructed by the processor to play the audio content generated by the processor so that a nearby user can hear a voice issuing a warning. Alternatively or in addition, in response to determining that the user may be in a pathological state, the processor can be configured to instruct a processing device (such as the games console 300 comprising one or more cameras 1260) to transmit at least an image signal comprising one or more images of the user wearing the HMD to a processing device of another user. This means that successive images captured by the one or more cameras 1260 can be communicated to another user and the other user can see whether or not the user wearing the HMD is in need of assistance. In this case, the other user may be in the same room as the user wearing the HMD, or the other user may, for example, be in a different country to the user wearing the HMD.

Figure 19:
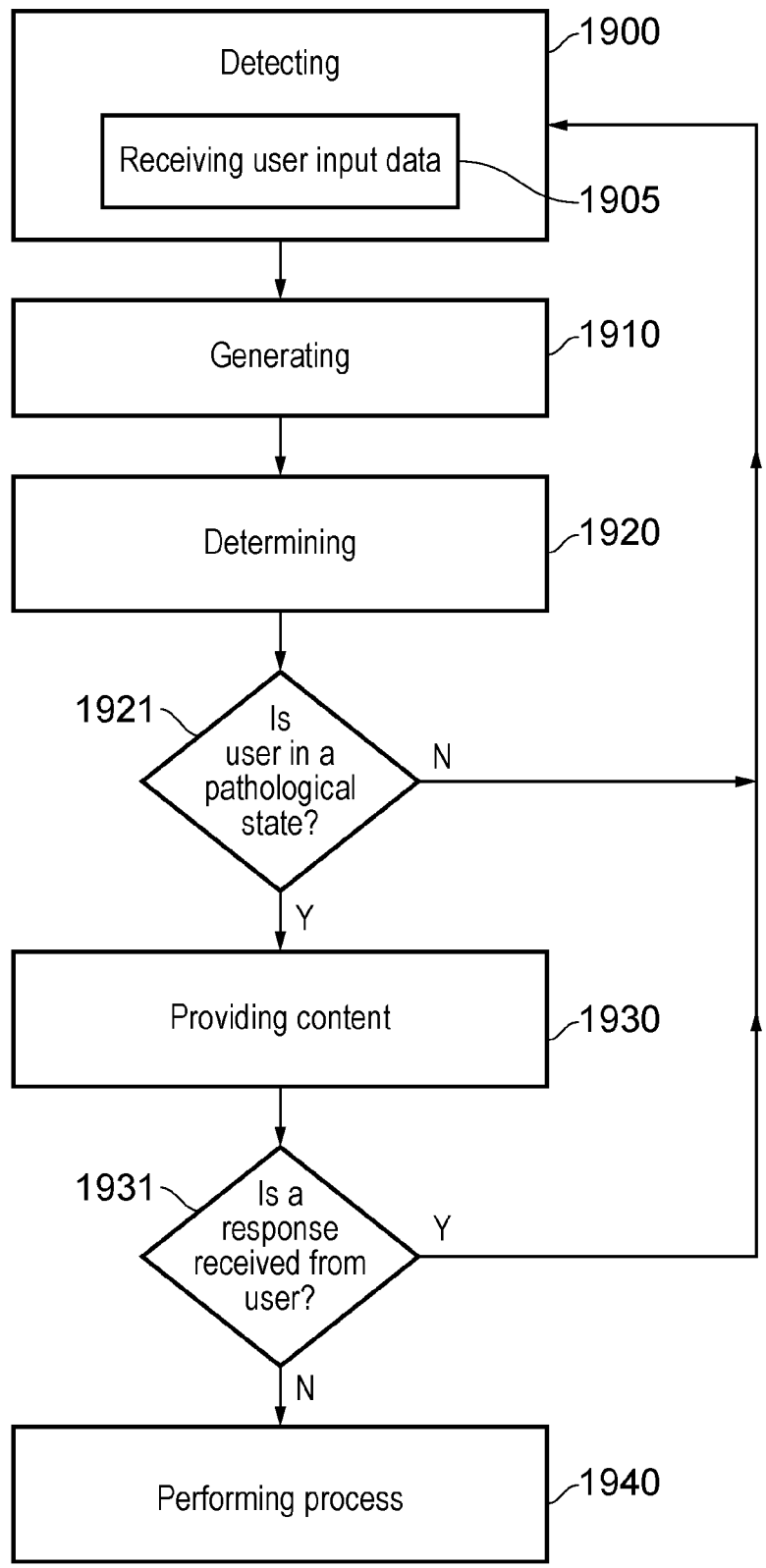
FIG. 19 is a schematic flowchart illustrating a method of assisting a user wearing an HMD.

FIG. 19 is a schematic flowchart illustrating a method of assisting a user wearing an HMD comprising receiving input data entered by the user for interacting with a content, the method comprising:

detecting (at a step 1900), by one or more sensors, one or more parameters indicating one or more current properties of the user;

receiving (at a step 1905) input data entered by the user for interacting with a content output by the HMD;

generating information (at a step 1910) indicating the one or more current properties of the user based on the one or more parameters;

determining (at a step 1920) whether the user may be in a pathological state or a non-pathological state based on a level of user activity, comprising determining the level of user activity based on the information indicating the one or more current properties of the user and the input data entered by the user or a lack thereof; and performing (at a step 1940) a process under instruction of a processor in response to determining that the user may be in a pathological state, the process comprising one or more operations that the user can voluntarily instruct or perform when the user is in a non-pathological state.

Alternatively or in addition, when it is determined, at the step 1920, that that the user may be in a pathological state, the step 1920 of determining may optionally comprise providing (at a step 1930) a content to the user requesting a response from the user within a predetermined period of time, and the step 1940 of performing a process under instruction of the processor may be performed in response to determining that the user may be in a pathological state and no response is received from the user within the predetermined period of time.

In embodiments of the disclosure input data entered by the user for interacting with a content output by the HMD can be received in addition to detecting one or more parameters indicating one or more current properties of the user. The input data may be entered by the user via one or more hand-held controllers 330 which may be, for example, Sony® Move® controllers which communicate wirelessly with the games console 300 and/or HMD 20. As such, a level of user activity can be determined based on both the input data entered by the user for interacting with content (e.g. a game) output by the HMD and one or more detected parameters indicating one or more current properties of the user.

The frequency with which input data is required to be entered by the user for interaction with the content may vary depending on the properties of the content. For example, some games may require a greater level of user interaction than others and may thus require the user to enter input data more frequently. Therefore, the frequency with which input data is expected to be entered by the user may vary depending on the content. The input data entered by the user can be compared with an expected-input-data parameter to determine the user's level of interaction with the content, wherein the expected-input-data parameter is dependent on the properties of the content. Hence the user's level of interaction with the content can be determined, and a level of user activity can be determined based on the user's level of interaction with the content and the information indicating the one or more current properties of the user detected by the one or more sensors 1200. The level of user activity may be determined with the user's level of interaction and the information indicating the one or more current properties being given equal significance (equal weighting). Alternatively or in addition, the user's level of interaction with the content may be given a greater significance (larger weighting) for content where a high level of user interaction is expected, and the user's level of interaction may be given a reduced significance (smaller weighting) where a low level of user interaction is expected.

In embodiments of the disclosure, an eye-tracking camera 1230 may be used to determine where the user is looking within the display. The system can calculate what element(s) of the display are being shown at a given time, and whether the user is looking at them, tracking them, or progressing through them, as appropriate to the displayed features (e.g. reticule, target and text, respectively). It will be appreciated that any suitable visual stimulus may be considered, such as the presentation of text, the appearance of an enemy or comrade, and/or an explosion or the like. Similarly, changes in brightness of the displayed environment/user interface can be monitored to check for a corresponding responsiveness in pupil dilation. If pupil dilation does not appear responsive to within predetermined norms, then the system may, for example, pause the game and present a low-brightness UI, followed by a bright screen, to maximise the scope for detecting pupil response. A lack of response, or a slow response outside predetermined norms, may be indicative of an altered state of consciousness, or possibly other conditions, such as a stroke. Hence in practice the system may act to capture an image of at least one eye of the user, calculate where the user is looking within the HMD, calculate an accuracy with which the user is tracking a point of interest displayed by the HMD, and if the accuracy is below a predetermined threshold, determine that the user may be in a pathological state.

Figure 20A:
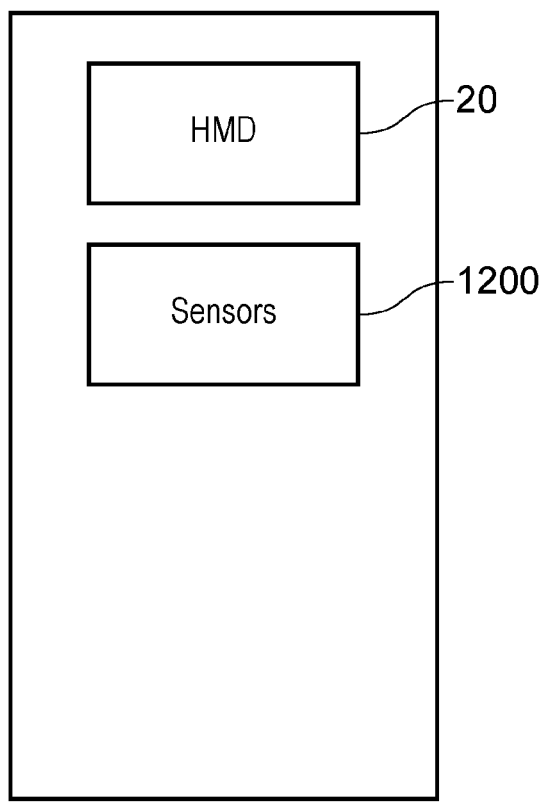
FIGS. 20a and 20b each schematically illustrate an apparatus for assisting a user wearing an HMD
Figure 20B:
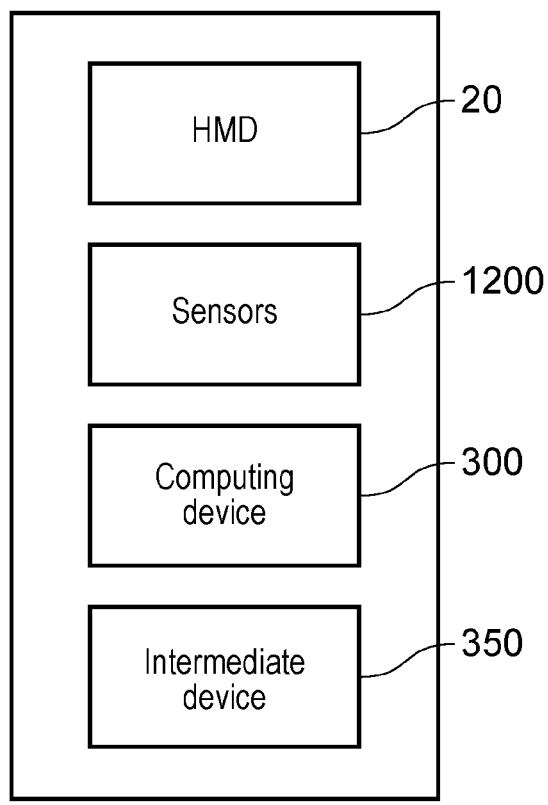

Turning now to FIGS. 20a and 20b, in embodiments of the disclosure, an apparatus for assisting a user wearing an HMD when determining that the user may be in a pathological state is provided. The apparatus comprises:

one or more sensors 1200 configured to detect one or more parameters indicating one or more current properties of the user 10 wearing the HMD 20;

a processor 300, 350, 20 configured to generate information indicating the one or more current properties of the user based on the one or more parameters and to determine whether the user may be in a pathological state or a non-pathological state based on the information; and an HMD 20 configured to perform a process under instruction of the processor in response to determining that the user may be in a pathological state, the process comprising one or more operations that the user can voluntarily instruct when the user's body is in a non-pathological state.

In embodiments of the disclosure, each of the one or more sensors 1200 of the apparatus is configured to communicate data indicative of the one or more parameters to the processor 300, 350, 20 via a wired or wireless communication and the processor can generate information indicating one or more current properties of the user based on the one or more parameters. The processor can determine whether the user may be in a pathological state or a non-pathological state based on the information and the processor can be configured to instruct the HMD 20 to perform a process. For example, the processor may be provided as part of the HMD 20 or may be provided separate to the HMD as part of the games console 300 or the intermediate device 350, and the processor may communicate data comprising one or more instructions to the HMD via a wired or wireless communication. As such, the processor can be configured to instruct the HMD to perform a process by communicating a signal comprising one or more instructions to the HMD such that the HMD can perform a process comprising one or more operations under instruction of the processor 300, 350, 20.

FIG. 20a schematically illustrates an apparatus for assisting a user wearing an HMD when determining that the user may be in a pathological state, comprising an HMD and one or more sensors. The apparatus comprises one or more sensors 1200 that detect one or more parameters indicating one or more current properties of the user, and the one or more sensors can communicate data indicative of the one or more parameters to the processor of the HMD 20 via a wired or wireless communication. The one or more sensors 1200 may be provided as part of the HMD 20 or separate to the HMD 20 or a combination thereof, and the processor of the HMD 20 can be configured to generate the information indicating the one or more current properties of the user based on the one or more parameters detected by the one or more sensors. The processor of the HMD 20 can then determine whether the user may be in a pathological state or a non-pathological state based on the information and the HMD can perform a process under instruction of the processor provided as part of the HMD.

FIG. 20*b* schematically illustrates an apparatus for assisting a user wearing an HMD when determining that the user may be in a pathological state, the apparatus comprising: an HMD; one or more sensors; a computing device; and an intermediate device. The apparatus comprises one or more sensors 1200 that may be provided as part of the HMD 20 or separate to the HMD 20 or a combination thereof. The one or more sensors may communicate data indicative of the one or more parameters to any of the HMD 20, the computing device 300 or the intermediate device 350. A processor of any of the HMD 20, the computing device 300 or the intermediate device 350 can generate information indicating the one or more current properties of the user and can also determine whether the user may be in a pathological state or a non-pathological state. For example, a given sensor may detect one or more parameters and communicate data indicative of the one or more parameters to the HMD 20, the computing device 300 and the intermediate device 350 and processing tasks can be shared amongst the respective devices 20, 300, 350. The generated information can be communicated either via a wired or wireless communication link between respective devices 20, 300, 350 in order to share the generated information amongst the respective devices. In some examples, the processor responsible for generating the image and/or audio output of the HMD may be provided as part of the computing device 300 or the intermediate device 350, and the processor 300, 350 responsible for generating the output of the HMD may instruct the HMD to perform a process comprising one or more operations by communicating data comprising one or more Instructions to the HMD.

In embodiments of the disclosure, the one or more sensors 1200 of the apparatus illustrated in FIG. 20*a* and FIG. 20*b* comprise one or more from the list consisting of: a temperature sensor 1210; a heart rate sensor 1220; an eye tracking camera 1230; an electrodermal activity sensor 1240; a motion detector 1250; and a camera 1260, configured to detect the one or more parameters indicating the one or more current properties of the user.

In the manner described previously, the processor can then generate information regarding the user based on comparing the one or more detected parameters with one or more reference values associated with one or more properties.

Similarly, the processor can receive input data entered by the user for interacting with a content output by the HMD.

Finally, the processor can determine a level of user activity based on at least one of the information indicating the one or more current properties of the user and the input data entered by the user to determine whether the user's body may be in a pathological state based on the level of activity.

It will be apparent to a person skilled in the art that variations in the above method corresponding to operation of the various embodiments of the apparatus as described and claimed herein are considered within the scope of the present invention. It will be appreciated that example embodiments can be implemented by computer software operating on a general purpose computing system such as a games machine. In these examples, computer software, which when executed by a computer, causes the computer to carry out any of the methods discussed above is considered as an embodiment of the present disclosure. Similarly, embodiments of the disclosure are provided by a non-transitory, machine-readable storage medium which stores such computer software.

It will be appreciated that whilst the apparatus and methods described herein are operable to compare one or more sensor readings, either to determine a deviation from a reference (healthy or at rest) reading or combination of readings, and/or to determine a similarity to a pathological reading or readings, the apparatus and methods described herein are not capable of diagnosing a condition within the user.

For example, it will be appreciated that many of the parameters described herein are common to multiple specific pathologies, and consequently information about a property of the user based on one or more of such parameters cannot provide a diagnosis of a particular pathology beyond a general indication that the player may need assistance to perform a function they would normally perform themselves, such as terminating a VR experience and/or alerting someone to assist further.

Hence if a user is unresponsive or their behaviour is outside predetermined norms, the cause of that unresponsiveness or behaviour cannot be clearly identified, much less determined to a clinically rigorous standard—however, the lack of response or abnormal behaviour as such can be detected, and optionally, following a request for interaction with the user that does not then occur, this lack of response may trigger a function of the device that the user could otherwise voluntarily perform, such as exiting the current virtual reality experience, transmitting a signal or message to a predetermined party indicating distress or medical need, and/or causing an audible alarm. Meanwhile, these operations in turn are not medical interventions in themselves, even if they cause medical interventions to be requested.

It will also be apparent that numerous modifications and variations of the present disclosure are possible in light of the above teachings. It is therefore to be understood that within the scope of the appended claims, the disclosure may be practised otherwise than as specifically described herein.

The invention claimed is:

1. A method of assisting a user wearing a head mountable display (HMD) when determining that the user may be in a pathological state, the method comprising the steps of:

detecting, by one or more sensors, one or more parameters indicating one or more current properties of the user, wherein the step of detecting comprises a step of receiving input data entered by the user for interacting with a content output by the HMD;

generating information indicating the one or more current properties of the user based on the one or more parameters;

determining whether the user may be in a pathological state or a non-pathological state based on the information indicating one or more of the current properties of the user, wherein the step of determining comprises: (i) determining a level of user interaction with the content based on the input data entered by the user, or a lack thereof, (ii) determining a level of user activity based on the information indicating the one or more current properties of the user and the level of user interaction with the content, and (iii) determining whether the user may be in a pathological state based on the level of user activity; and performing a process under instruction of a processor in response to determining that the user may be in a pathological state, the process comprising one or more operations that the user can voluntarily instruct when the user is in a non-pathological state, wherein, when a result of the determining step is that the user may be in a pathological state, the HMD provides a content to the user requesting a response from the user within a predetermined period of time, and when no response is received from the user within the predetermined period of time, performing the process under instruction of the processor.

2. A method according to claim 1, wherein the step of determining whether the user may be in a pathological state or a non-pathological state comprises comparing one or more of the current properties of the user with one or more reference values associated with one or more properties.

3. A method according to claim 1, wherein the step of performing the process comprises the step of:
communicating a signal to a communication device indicating that the user is experiencing a medical emergency.

4. A method according to claim 3, wherein the step of performing the process comprises the step of:
selecting the communication device from a plurality of communication devices according to in-case-of-emergency contact information.

5. A method according to claim 1, wherein the one or more operations comprise one or more of:
terminating a content that is currently output by the HMD;
outputting an audio signal for alerting another user; and
instructing a processing device to transmit at least an image signal comprising one or more images of the user wearing the HMD to a processing device of another user.

6. A method according to claim 1, wherein the one or more current properties comprise one or more of:
an acceleration of the user's head;
an orientation of the user's head;
a position of the user's head;
an average motion of the user's head;
an acceleration of the user's body;
an orientation of the user's body;
a position of the user's body;
an average motion of the user's body.

7. A method according to claim 1, wherein the one or more properties comprise one or more physiological properties of:
a beating rate of the user's heart;
a pattern of the beating rate of the user's heart;
a direction of the user's gaze;
a pattern of the direction of the user's gaze;
a dilation of at least one of the user's pupils;
a conductance of the user' skin; and
a temperature of the user's body.

8. A method according to claim 1, wherein when detecting at least one of an acceleration of the user's head that is greater than a predetermined threshold indicating an impact with an external object and a position of the user's head indicating the user's head is proximate to an approximately horizontal resting surface, the step of determining comprises the step of:
presenting a content to the user requesting a response from the user within a predetermined period of time.

9. A method according to claim 1, comprising the steps of:
capturing an image of at least one eye of the user;
calculating where the user is looking within the HMD;
calculating an accuracy with which the user is tracking a point of interest displayed by the HMD, and if the accuracy is below a predetermined threshold, determining that the user may be in a pathological state.

10. A method according to claim 1, wherein the one or more pathological states comprise one or more of:
a heart attack;
a stroke;
a seizure;
an asthma attack;
a panic attack;
syncope; and
an altered state of consciousness.

11. A method according to claim 10, wherein the seizure is an epileptic seizure.

12. A non-transitory machine-readable storage medium which stores computer software, which when executed by a computer, cause the computer to assist a user wearing a head mountable display (HMD) when determining that the user may be in a pathological state, by carrying out actions, comprising:
detecting, by one or more sensors, one or more parameters indicating one or more current properties of the user, wherein the step of detecting comprises a step of receiving input data entered by the user for interacting with a content output by the HMD;
generating information indicating the one or more current properties of the user based on the one or more parameters;
determining whether the user may be in a pathological state or a non-pathological state based on the information indicating one or more of the current properties of the user, wherein the step of determining comprises: (i) determining a level of user interaction with the content based on the input data entered by the user, or a lack thereof, (ii) determining a level of user activity based on the information indicating the one or more current properties of the user and the level of user interaction with the content, and (iii) determining whether the user may be in a pathological state based on the level of user activity; and
performing a process under instruction of a processor in response to determining that the user may be in a pathological state, the process comprising one or more operations that the user can voluntarily instruct when the user is in a non-pathological state,
wherein, when a result of the determining step is that the user may be in a pathological state, the HMD provides a content to the user requesting a response from the user within a predetermined period of time, and when no response is received from the user within the predetermined period of time, performing the process under instruction of the processor.

13. An apparatus for assisting a user wearing a head mountable display (HMD) when determining that the user may be in a pathological state, the apparatus comprising:
one or more sensors configured to detect one or more parameters indicating one or more current properties of the user, wherein the detecting, by the one or more sensors, includes receiving input data entered by the user for interacting with a content output by the HMD;
a processor configured to generate information indicating the one or more current properties of the user based on the one or more parameters and to determine whether the user may be in a pathological state or a non-pathological state based on the information; and an HMD configured to perform a process under instruction of the processor in response to determining that the user may be in a pathological state, the process comprising one or more operations that the user can voluntarily instruct when the user's body is in a non-pathological state, wherein the determining includes: (i) determining a level of user interaction with the content based on the input data entered by the user, or a lack thereof, (ii) determining a level of user activity based on the information indicating the one or more current properties of the user and the level of user interaction with the content, and (iii) determining whether the user may be in a pathological state based on the level of user activity, wherein, when a result of the determination is that the user may be in a pathological state, the HMD provides a content to the user requesting a response from the user within a predetermined period of time, and when no response is received from the user within the predetermined period of time, the process is performed under instruction of the processor.

14. An apparatus according to claim 13, wherein the processor is configured to generate the information by comparing the one or more detected parameters with one or more reference values associated with one or more properties.

15. An apparatus according to claim 13, wherein the processor is configured to receive input data entered by the user for interacting with a content output by the HMD.

16. An apparatus according to claim 15, wherein the processor is configured to determine a level of user activity based on at least one of the information indicating the one or more current properties of the user and the input data entered by the user to determine whether the user's body may be in a pathological state based on the level of activity.

* * * * *